US012036344B2

(12) United States Patent
Kotanko et al.

(10) Patent No.: US 12,036,344 B2
(45) Date of Patent: Jul. 16, 2024

(54) SYSTEMS AND METHODS FOR ANALYZING SPENT DIALYSATE

(71) Applicant: FRESENIUS MEDICAL CARE HOLDINGS, INC., Waltham, MA (US)

(72) Inventors: Peter Kotanko, New York, NY (US); Xia Tao, West New York, NJ (US); Mia G. Garbaccio, Astoria, NY (US); Jeffrey Hymes, Nashville, TN (US); Stephan Thijssen, New York, NY (US); Nadja Grobe, Huntington, NY (US); Leticia M. Tapia Silva, Long Island City, NY (US); Dinesh K. Chatoth, Suwanee, GA (US)

(73) Assignee: FRESENIUS MEDICAL CARE HOLDINGS, INC., Waltham, MA (US)

( * ) Notice: Subject to any disclaimer, the term of this patent is extended or adjusted under 35 U.S.C. 154(b) by 290 days.

(21) Appl. No.: 17/097,299

(22) Filed: Nov. 13, 2020

(65) Prior Publication Data

US 2022/0152282 A1 May 19, 2022

(51) Int. Cl.
*A61M 1/28* (2006.01)
*A61M 1/00* (2006.01)
*A61M 1/16* (2006.01)

(52) U.S. Cl.
CPC ........ *A61M 1/1619* (2014.02); *A61M 1/1643* (2014.02); *A61M 1/28* (2013.01);
(Continued)

(58) Field of Classification Search
CPC .......... A61M 1/28; A61M 1/287; A61M 1/14; A61M 1/16; A61M 1/281; A61M 1/284; A61M 1/285; A61M 1/288; A61M 1/1668
See application file for complete search history.

(56) References Cited

U.S. PATENT DOCUMENTS 5,782,796 A * 7/1998 Din .................. A61M 1/28
604/27
6,228,047 B1 5/2001 Dadson
(Continued)

FOREIGN PATENT DOCUMENTS

CN 104316527 A 1/2015
CN 108211030 A 6/2018
(Continued)

OTHER PUBLICATIONS

Davenport, "Portable and wearable dialysis devices for the treatment of patients with 1-8 end-stage kidney failure: Wishful thinking or just over the horizon?", Springerlink.com, Oct. 24, 2014, retrieved on [Apr. 21, 2021]. Retrieved from the Internet <URL: https://link.springer.com/contenUpdf/10.1007/s00467-014-2968-3.pdf>.
(Continued)

*Primary Examiner* — Courtney B Fredrickson
(74) *Attorney, Agent, or Firm* — Lando & Anastasi, LLP

(57) ABSTRACT

An apparatus used in analyzing spent dialysate includes: at least one surface configured to accommodate a dialysate drain bag or drain line in a predetermined position; a light source positioned to emit light through the dialysate drain bag or drain line; and a light sensor positioned to sense light emitted by the light source through the dialysate drain bag or drain line.

17 Claims, 27 Drawing Sheets

(52) U.S. Cl.
CPC ....... *A61M 1/69* (2021.05); *A61M 2202/0439* (2013.01); *A61M 2202/0486* (2013.01); *A61M 2205/18* (2013.01); *A61M 2205/3327* (2013.01); *A61M 2205/3592* (2013.01); *A61M 2205/583* (2013.01); *A61M 2205/587* (2013.01)

(56) References Cited

U.S. PATENT DOCUMENTS

| | | | |
|---|---|---|---|
| 7,236,201 | B1 | 6/2007 | Gershenson |
| 7,559,913 | B1 | 7/2009 | Jeppsson et al. |
| 7,789,850 | B2 | 9/2010 | Roger |
| 8,728,023 | B2 | 5/2014 | Andherr et al. |
| 8,777,891 | B2 | 7/2014 | Andherr et al. |
| 8,801,652 | B2 | 8/2014 | Andherr et al. |
| 2003/0236452 | A1* | 12/2003 | Melker ................ A61B 5/0873 600/323 |
| 2005/0126961 | A1* | 6/2005 | Bissler ................ A61M 1/1647 210/97 |
| 2006/0249999 | A1 | 11/2006 | Bergin |
| 2008/0045884 | A1 | 2/2008 | Landherr et al. |
| 2008/0183127 | A1 | 7/2008 | Andherr et al. |
| 2009/0149776 | A1 | 6/2009 | Adams |
| 2009/0212178 | A1 | 8/2009 | Westberg |
| 2009/0238423 | A1 | 9/2009 | Rigler |
| 2012/0258545 | A1 | 10/2012 | Ash et al. |
| 2014/0276375 | A1 | 9/2014 | Minkus |
| 2016/0216150 | A1* | 7/2016 | Groeber ................ A61M 1/28 |
| 2017/0029776 | A1* | 2/2017 | Cork ................ A61M 1/3681 |
| 2017/0136166 | A1* | 5/2017 | Chen ................ A61M 1/282 |
| 2019/0060629 | A1 | 2/2019 | Norris et al. |
| 2019/0358387 | A1* | 11/2019 | Elbadry ................ G01N 15/06 |
| 2019/0381229 | A1 | 12/2019 | Biewer et al. |
| 2019/0381231 | A1* | 12/2019 | Tsoory ................ A61M 1/28 |

FOREIGN PATENT DOCUMENTS

| | | |
|---|---|---|
| EP | 3447471 A1 | 2/2019 |
| JP | 2014083369 A | 5/2014 |
| KR | 20140051167 A | 4/2014 |
| KR | 20150024405 A | 3/2015 |
| WO | 2009076240 A2 | 6/2009 |
| WO | 2010000445 A1 | 1/2010 |
| WO | 2014047608 A1 | 3/2014 |
| WO | 2014137333 A1 | 9/2014 |
| WO | 2017089801 A1 | 6/2017 |
| WO | 2017136088 A1 | 8/2017 |
| WO | 2018060708 A1 | 4/2018 |
| WO | 2019118929 A1 | 6/2019 |

OTHER PUBLICATIONS

International Search Report and Written Opinion from corresponding International Application PCT/US2021/058754 dated Mar. 7, 2022.

* cited by examiner

SYSTEMS AND METHODS FOR ANALYZING SPENT DIALYSATE

BACKGROUND

Peritoneal dialysis is a renal replacement therapy for patients who suffer from renal disease. Techniques for peritoneal dialysis include Continuous Ambulatory Peritoneal Dialysis (CAPD) and Automated Peritoneal Dialysis (APD). CAPD is performed on an ongoing basis and spent dialysate drains into a drain bag that is later discarded and replaced. APD uses a cycler to deliver and drain the dialysate, typically while the patient is stationary (e.g., while sleeping). In APD, spent dialysate may drain into a bag, a sink, or another location.

Because peritoneal dialysis uses the peritoneum, it is a risk factor for peritonitis. For example, peritoneal dialysis may inadvertently introduce bacteria to the abdomen. By some measures, there is about one incident of peritonitis per 24 to 48 patient-months. Peritonitis is a leading cause of mortality and treatment failure in peritoneal dialysis patients. Rapid diagnosis and treatment are essential for therapeutic success.

Because of the risks associated with peritonitis, it is important to monitor for symptoms and indicators of peritonitis in peritoneal dialysis patients. Indicators of peritonitis include, for example, increased white blood cell (WBC) counts and differentiation. Spent dialysate (e.g., in a drain bag) may provide indicators of peritonitis. When peritonitis is sufficiently advanced, those indicators may even be visible to the naked eye. For example, spent dialysate may appear cloudy. Cloudiness may be assessed by various manual techniques, such as placing a newspaper under the drain bag and evaluating whether the letters are hard to read. When spent dialysate appears cloudy, patients are encouraged to do another drain and bring the newly drained bag to a clinic for testing. In some cases, a patient may send a photo of the spent dialysate to a clinician, to obtain the clinician's subjective opinion based on its appearance. However, relying on such techniques means that peritonitis may not be detected until an infection is relatively advanced, particularly for patients with visual impairments that make it more difficult for them to subjectively assess the "cloudiness" of spent dialysate. By some estimates, over sixty percent of peritoneal dialysis patients have visual impairment.

As a reactive measure, patients may be placed on antibiotics before the clinician has a chance to properly test the spent dialysate. While the patient starts antibiotics, the clinician sends the spent dialysate to a lab, where it is inspected for white blood cell counts and bacteria. Depending on the lab results, the clinician may continue, discontinue, or change the patient's antibiotic treatment. Thus, traditional methods of monitoring for peritonitis are reactive, inefficient, and may delay appropriate medical treatment. In addition, traditional methods may result in unnecessary and/or partial antibiotic treatments in cases of false positives.

One or more approaches described herein may incorporate findings and techniques described in (a) Carlson, D., & Van Brackle, C. *Particle Sizing with a Smartphone* (2014), and/or (b) Yang, Ye, et al. "Blood cell counting and classification by nonflowing laser light scattering method." *Advanced Photonic Sensors and Applications*. Vol. 3897. International Society for Optics and Photonics, 1999, both of which are incorporated herein by reference in their entirety.

Approaches described in this section have not necessarily been conceived and/or pursued prior to the filing of this application. Accordingly, unless otherwise indicated, approaches described in this section should not be construed as prior art.

SUMMARY

One or more embodiments allow for earlier diagnosis of peritonitis than traditional approaches. Systems and methods described herein allow for point-of-care (e.g., at home) analysis of spent dialysate, by detecting indicators (e.g., white blood cell counts, differentiation, and/or bacteria) associated with peritonitis. Techniques described herein may detect such indicators even when the patient is not experiencing or aware of related symptoms (e.g., abdominal pain). Early diagnosis may allow for faster treatment of peritonitis, while avoiding inappropriate treatments in cases of false positives. Techniques described herein allow a patient to monitor for peritonitis using objective measurements, rather than relying on subjective observations such as "cloudiness." For example, one or more embodiments provide an apparatus that helps ensure consistent measurement conditions over multiple uses. In addition, techniques described herein may be combined with other medical monitoring and diagnostic techniques, to provide a multi-featured tool for monitoring peritoneal dialysis patients. Moreover, one or more embodiments may be used to analyze spent dialysate during and/or after a course of antibiotic treatment, to predict or evaluate the effectiveness of the treatment. One or more embodiments include an apparatus with one or more integrated light source(s) and/or light sensor(s). Alternatively or additionally, one or more embodiments make use of a smartphone, tablet, or other computing device already in a patient's possession, thus reducing the cost that might otherwise be associated with techniques described herein. Techniques described herein may be performed in a matter of seconds (e.g., about 30-40 seconds), in comparison to traditional techniques that require contact with a clinician's office and possibly also sending spent dialysate to a lab for analysis.

In general, in one aspect, an apparatus includes: at least one surface configured to accommodate a dialysate drain bag or drain line in a predetermined position; a light source positioned to emit light through the dialysate drain bag or drain line; and a light sensor positioned to sense light emitted by the light source through the dialysate drain bag or drain line. The light source may have an adjustable position to accommodate placement of the dialysate drain bag or drain line in the predetermined position.

The apparatus may further include one or more processors and one or more non-transitory computer-readable media storing instructions that, when executed by the one or more processors, cause the one or more processors to perform operations including: analyzing spent dialysate in the dialysate drain bag or drain line, based at least on the light sensed by the light sensor. The apparatus may further include a display, and the operations may further include presenting an alert on the display when the spent dialysate satisfies an alert condition. The apparatus may further include a scale configured to measure a weight of the dialysate drain bag when the dialysate drain bag is in the predetermined position, analyzing the spent dialysate being further based on the weight of the dialysate drain bag. Analyzing the spent dialysate may include one or more of: measuring turbidity of the spent dialysate; estimating glucose concentration in the spent dialysate; estimating a proportion of white blood cells in the spent dialysate; or estimating a proportion of polymorphonuclear cells in the spent dialysate. Analyzing the spent dialysate may include estimating a risk of peritonitis. Analyzing the spent dialysate may include transmitting data to a server and receiving an analysis result from the server.

The apparatus may further include a scale configured to measure a weight of the dialysate drain bag when the dialysate drain bag is in the predetermined position. The light sensor may be one of a multiple light sensors collectively configured to sense light at a multiple wavelengths. The wavelengths may correspond to two or more of near-infrared, ultraviolet, visible, or fluorescent light.

In general, in another aspect, a method includes: accommodating, by an apparatus, a dialysate drain bag or drain line in a predetermined position, the dialysate drain bag or drain line including spent dialysate; emitting, by a light source of the apparatus, light through the dialysate drain bag or drain line; sensing, by a light sensor of the apparatus, light emitted through the dialysate drain bag or drain line; and determining, by the apparatus, a risk of peritonitis based at least on the light sensed by the light sensor. The method may further include determining a weight of the dialysate drain bag, determining the risk of peritonitis being further based on the weight of the dialysate drain bag.

Determining the risk of peritonitis may include measuring turbidity of the spent dialysate. Determining the risk of peritonitis may include estimating a proportion of white blood cells in the spent dialysate. Determining the risk of peritonitis may include estimating a proportion of polymorphonuclear cells in the spent dialysate. Estimating the proportion of polymorphonuclear cells in the spent dialysate may include analyzing light scattering data obtained by the light sensor. The method may further include estimating fluorescence intensity at one or more of multiple wavelengths or multiple spectrums. The method may further include obtaining a baseline light reading for the light sensor, and determining the risk of peritonitis may include determining a difference between the baseline light reading and the light emitted through the dialysate drain bag or drain line. Analyzing the spent dialysate may include transmitting data to a server and receiving an analysis result from the server.

One or more embodiments described in this Specification and/or recited in the claims may not be included in this General Overview section.

BRIEF DESCRIPTION OF THE DRAWINGS

Various aspects of at least one embodiment are discussed below with reference to the accompanying Figures, which are not intended to be drawn to scale. The Figures are included to provide illustration and a further understanding of the various aspects and embodiments, and are incorporated in and constitute a part of this specification, but are not intended to define the limits of the disclosure. In the Figures, each identical or nearly identical component that is illustrated in various Figures is represented by a like numeral. For the purposes of clarity, some components may not be labeled in every figure. In the Figures:

FIG. 2I is an illustration of a bottom-up view of the apparatus of FIG. 2A according to an embodiment;

DETAILED DESCRIPTION

The following table of contents is provided for the reader's convenience and is not intended to define the limits of the disclosure.

1. SYSTEM CONFIGURATIONS
2. ANALYZING SPENT DIALYSATE IN A DRAIN BAG
   3.1. APPARATUS
   3.2. METHOD
   3.3. USER INTERFACE
3. ANALYZING SPENT DIALYSATE IN A DRAIN LINE
   3.1. APPARATUS
   3.2. METHOD
4. USER INTERFACE FOR PATIENT TRACKING
5. MISCELLANEOUS; EXTENSIONS
6. COMPUTING DEVICES
7. COMPUTER NETWORKS
8. CONNECTED HEALTH SYSTEM

1. System Configurations

Figure 1A:
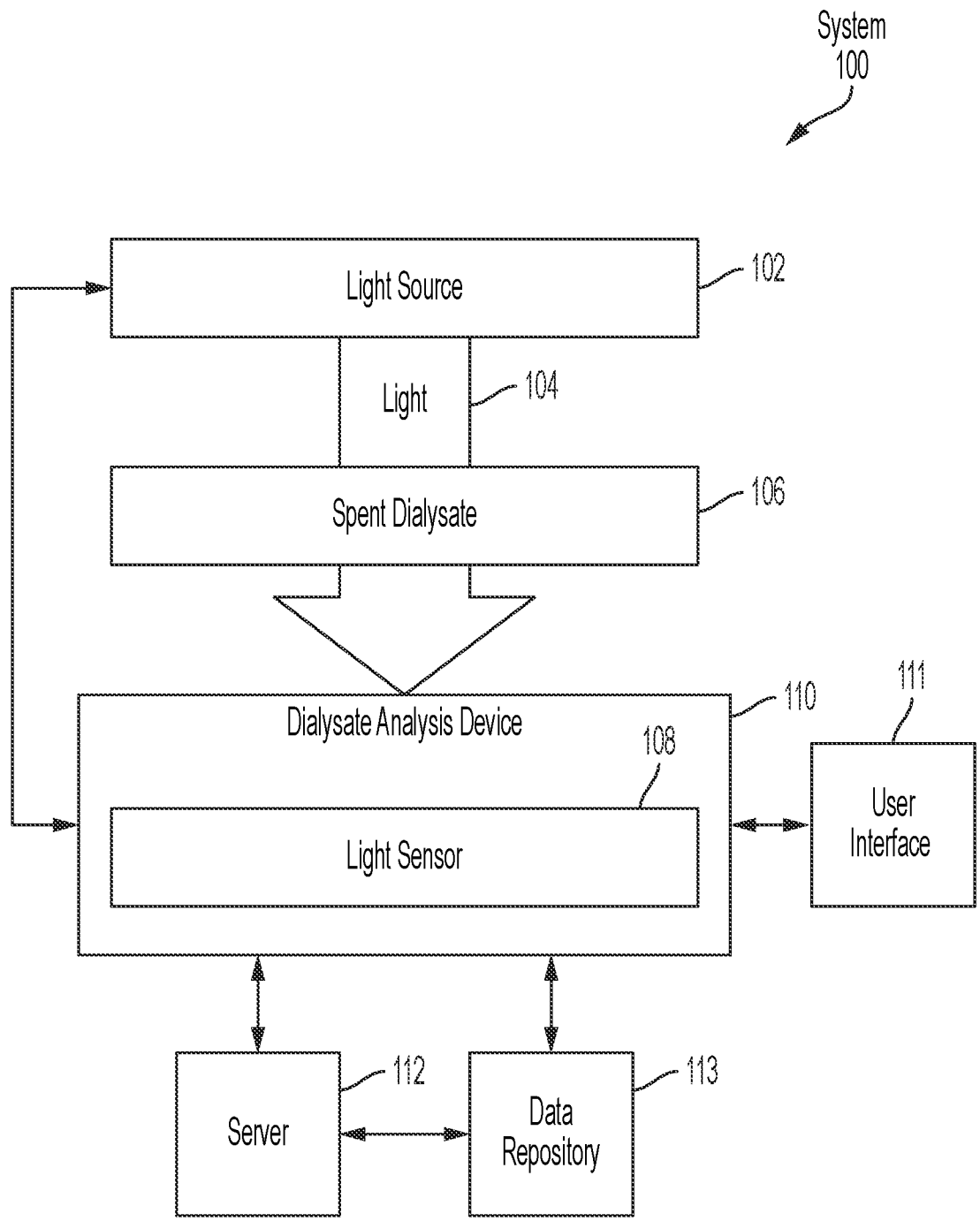
FIG. 1A-1B are block diagrams of examples of systems according to an embodiment.
Figure 1B:
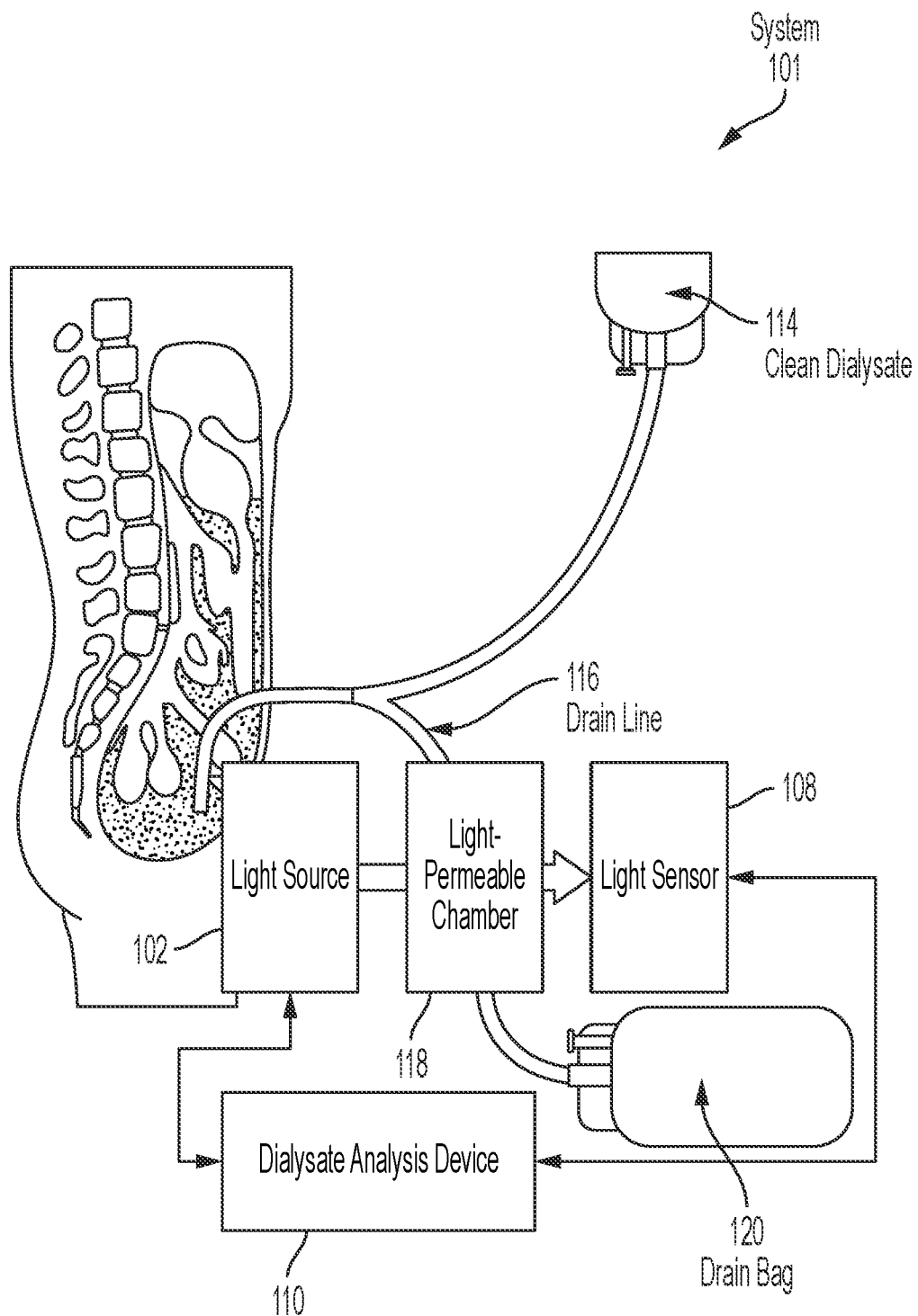

In general, one or more embodiments include a point-of-care (POC) system configured to analyze spent peritoneal dialysate. FIGS. 1A-1B are block diagrams of examples of systems according to an embodiment. A system may include more or fewer components than illustrated in the examples of FIGS. 1A-1B. Components illustrated in these examples may be local to or remote from each other. Components illustrated in these examples may be implemented in software and/or hardware. Each component may be distributed over multiple applications and/or machines. Multiple components may be combined into one application and/or machine. Operations described with respect to one component may instead be performed by another component.

As illustrated in FIG. 1A, an example of a system 100 includes a light source 102 configured to emit light 104 through spent dialysate 106. For example, the spent dialysate 106 may be located in a drain bag or along a drain line. The light source 102 may be ambient light (e.g., sunlight and/or one or more general-purpose lamps) in the environment where the system 100 is located. Alternatively, the light source 102 may be a dedicated light source used in analyzing spent dialysate. For example, the light source 102 may include one or more light emitting diodes (LED's) and/or lasers housed in an apparatus, such as one of the example apparatuses described herein. A dedicated light source 102 may provide a relatively consistent direction, magnitude, and/or wavelength(s) of light emittance and thus improve the quality and consistency of light readings used in spent dialysate analysis, relative to relying on ambient light.

In an embodiment, the light source 102 is configured to emit a single wavelength of light through the spent dialysate 106. Alternatively, the light source 102 may be configured to emit multiple wavelengths of light. The light source 102 may be configured to emit light at about 1300 nm, about 810 nm, and/or about 660 nm. Light emitted at about 1300 nm may be used for calibration, e.g., by emitting light through clear water or clean dialysate (not shown). Light emitted at about 810 nm may be used to detect hemoglobin in the spent dialysate 106. Light emitted at about 660 nm may be used to detect white blood cells in the spent dialysate 106. One or more other wavelengths may be used. In an embodiment, the light source 102 is configured to emit near-infrared light, which may be used to detect glucose concentrate in dialysate, as described in further detail below.

In an embodiment, a light sensor 108 is configured to sense light passing through the spent dialysate 106. Specifically, the light sensor 108 is configured to sense light transmittance through the spent dialysate 106. The light sensor 108 may be positioned approximately opposite the light source 102, with the spent dialysate 106 disposed between them. Some embodiments may perform better (i.e., obtain more reliable light measurements) if the system 100 is placed in a relatively dark environment, such as a dark room and/or by placing the light sensor 108 within an enclosure that substantially blocks light from sources other than the light source 102. In some examples, the light source 102 and light sensor 108 both are integrated into a single apparatus, as described in examples herein.

In an embodiment, a dialysate analysis device 110 (or, in some examples, hardware, firmware, and/or software integrated in an apparatus that includes the light source 102 and light sensor 108) is configured to use data from the light sensor 108 to analyze the spent dialysate 106. If separate from the apparatus, the dialysate analysis device 110 may be a multi-purpose computing device, such as a smartphone, tablet, laptop computer, desktop computer, or other type of multi-purpose device. For example, the dialysate analysis device 110 may be configured to execute an installable application that includes instructions for analyzing spent dialysate 106 based on data from a light sensor 108. Alternatively, the dialysate analysis device 110 may be a special-purpose medical device configured to analyze spent dialysate 106. For example, the dialysate analysis device 110 may be part of a peritoneal dialysis (PD) cycler and/or other type of dialysis equipment.

In an embodiment, the light sensor 108 is part of the dialysate analysis device 110, as illustrated in FIG. 1A. For example, the light sensor 108 may be a camera or other type of light-sensing component that is part of a smartphone, tablet, or special-purpose medical device. Alternatively, the light sensor 108 may be physically separate from the dialysate analysis device 110. For example, the light sensor 108 may be part of an apparatus coupled with or near a clear section of drain line tubing, or coupled with or near a chamber positioned along the drain line, such as in the example illustrated in FIG. 6B. A physically separate light sensor 108 may be configured to communicate with the dialysate analysis device 110 via a cable (e.g., a uniform serial bus (USB) cable, Apple Lightning cable, Ethernet cable, and/or another type of cable) and/or via one or more wireless transmission protocols, such as Bluetooth® and/or Wi-Fi. A physically separate light sensor 108 may be helpful, for example, if the dialysate analysis device 110 includes a light-sensing component (e.g., a smartphone camera) but does not include an application programming interface (API) that allows sufficient access to data from the light-sensing component.

In an embodiment, the light source 102 and light sensor 108 are components of an apparatus that is configured to accommodate (e.g., on a tray, as in the examples below, or in another manner) a dialysate drain bag containing the spent dialysate 106. References herein to a dialysate analysis device 110 may be interpreted as referring to hardware, firmware, and/or software integrated in the apparatus. For example, the apparatus may include one or more processors and one or more non-transitory computer-readable media storing instructions that are executable by the processor(s), to analyze the spent dialysate 106 and/or perform other dialysis-related functions. Some non-limiting examples of such an apparatus are provided below. An apparatus with components integrated in this manner may make the apparatus more accessible to patients who do not have smartphones (or other similar devices as described herein) that could be used as an external dialysate analysis device, and/or who are not proficient at using smartphones.

In an embodiment, the dialysate analysis device 110 includes and/or is communicatively coupled with one or more additional hardware components that is/are configured to gather data associated with dialysis. Alternatively, one or more additional hardware components described herein may be integrated into the apparatus itself (for example, in embodiments that do not use a physically separate dialysate analysis device 110). For example, the dialysate analysis device 110 may include or be communicatively coupled with a microscope (not shown). The microscope may be part of a camera, a camera magnifying attachment, or a physically separate microscope device. For example, a smartphone attachment may be used to magnify a smartphone's camera by about 400 times or another suitable magnification factor. The dialysate analysis device 110 may use images from the microscope to help detect and analyze Gram-stained bacteria in the spent dialysate 106.

As another example, the dialysate analysis device 110 may include or be communicatively coupled with a proximity sensor (not shown). The dialysate analysis device 110 may use the proximity sensor to help detect placement of the dialysate analysis device 110 relative to an apparatus (e.g., the example apparatus 200 illustrated in FIG. 2A), and/or relative to a particular part of the apparatus (e.g., the device placement area 206 illustrated in FIG. 2A). The proximity sensor may detect proximity to a particular location based on a radio frequency identifier (RFID) chip, Bluetooth® transmitter, and/or other component of the apparatus.

As yet another example, the dialysate analysis device 110 may include or be communicatively coupled with a gyroscope (not shown). The dialysate analysis device 110 may use the gyroscope to detect movement of the dialysate analysis device 110, and may use movement data to generate visual and/or auditory instructions that help a patient or other human operator guide the dialysate analysis device 110 to a specific location (e.g., the device placement area 206 illustrated in FIG. 2A).

In an embodiment, the dialysate analysis device 110 is configured to combine data from multiple components. For example, the dialysate analysis device 110 may combine data from a gyroscope and a proximity sensor to generate visual and/or auditory instructions that help a patient or other human operator to guide the dialysate analysis device 100 to a specific location. One or more components of the dialysate analysis device 110, or communicatively coupled with the dialysate analysis device 110, may be used for multiple purposes. For example, the dialysate analysis device 110 may be configured to use data from a camera (e.g., a camera that is part of the dialysate analysis device 110 or physically separate from the dialysate analysis device 110) both for light sensing and to obtain images of lateral flow assay or dry chemistry test strips to be evaluated as described in further detail below.

In an embodiment, the dialysate analysis device 110 is configured to control operation of one or more components described herein, such as the light source 102 and/or light sensor 108. For example, the dialysate analysis device 110 may be configured to transmit an electrical signal to turn on the light source 102, turn off the light source 102, and/or change an operational parameter of the light source 102 (e.g., brightness, wavelength, etc.). As another example, the dialysate analysis device 110 may be configured to transmit an electrical signal to instruct the light sensor 108 to begin or stop sensing light. Application software executing in the dialysate analysis device 110 may determine whether and/or when to transmit electrical signals to control operation of such components. For example, application software may transmit an electrical signal responsive to user input (e.g., via user interface 111) instructing the dialysate analysis device 110 to begin a process for analyzing spend dialysate 106.

In an embodiment, a server 112 is located apart from the dialysate analysis device 110 (e.g., in a separate device and/or a data center communicatively coupled with the dialysate analysis device 110 via one or more network connections). The server 112 may be configured to perform one or more operations described herein for analyzing the spent dialysate 106 and/or performing other analysis functions related to dialysis (e.g., analyzing data from a camera, microscope, proximity sensor, gyroscope, and/or another type of data or combination thereof). The dialysate analysis device 110 may be configured to transmit data to the server 112 for analysis and receive analysis results from the server 112. One or more operations described herein as being performed by the dialysate analysis device 110 may instead be performed by the server 112.

In an embodiment, the dialysate analysis device 110 includes or is communicatively coupled with a user interface 111. A user interface 111 refers to hardware, firmware, and/or software configured to facilitate communications between a user and the dialysate analysis device 110. A user interface 111 renders user interface elements and receives input via user interface elements. A user interface 111 may be a graphical user interface (GUI), a command line interface (CLI), a haptic interface, a voice command interface, and/or any other kind of interface or combination thereof. Examples of user interface elements include checkboxes, radio buttons, dropdown lists, list boxes, buttons, toggles, text fields, date and time selectors, command lines, sliders, pages, and forms. Different components of the user interface 111 may be specified in different languages. The behavior of user interface elements may be specified in a dynamic programming language, such as JavaScript. The content of user interface elements may be specified in a markup language, such as hypertext markup language (HTML), Extensible Markup Language (XML), or XML User Interface Language (XUL). The layout of user interface elements may be specified in a style sheet language, such as Cascading Style Sheets (CSS). Alternatively or additionally, aspects of a user interface 111 may be specified in one or more other languages, such as Java, Python, Perl, C, C++, and/or any other language or combination thereof.

In an embodiment, the user interface 111 is configured to provide audio and/or visual cues, as described below. Audio and/or visual cues may be particularly helpful, for example, when a patient is visually impaired and would otherwise have difficultly positioning a drain bag and/or dialysate analysis device 110 for effective dialysate analysis. It should be noted that a patient with a visual impairment would be particularly unlikely to detect peritonitis at an early stage using the traditional "cloudiness" method.

In an embodiment, the dialysate analysis device 110 and/or server 112 is/are configured to store data in one or more data repositories 113. A data repository 113 is any type of storage unit and/or device (e.g., a file system, database, collection of tables, or any other storage mechanism) for storing data. A data repository 113 may include multiple different storage units and/or devices. The multiple different storage units and/or devices may or may not be of the same type or located at the same physical site. Further, a data repository 113 may be implemented or may execute on the same computing system as one or more other components of the system 100. Alternatively or additionally, a data repository 113 may be implemented or executed on a computing system separate from one or more other components of the system 100. A data repository 113 may be logically integrated with one or more other components of the system 100. Alternatively or additionally, a data repository 113 may be communicatively coupled to one or more other components of the system 100 via a direct connection or via a network. Alternatively or additionally, information may be implemented and/or distributed across any of the components of the system 100.

In an embodiment, the system 100 is located in a patient's home, to provide home-based point-of-care analysis of spent dialysate. Alternatively, the system 100 may be located in a clinical setting, such as a dialysis center or hospital.

In an embodiment, one or more components of the system 100 are implemented on one or more digital devices. The term "digital device" generally refers to any hardware device that includes a processor. A digital device may refer to a physical device executing an application or a virtual machine. Examples of digital devices include a computer, a tablet, a laptop, a desktop, a netbook, a server, a web server, a network policy server, a proxy server, a generic machine, a function-specific hardware device, a hardware router, a hardware switch, a hardware firewall, a hardware network address translator (NAT), a hardware load balancer, a mainframe, a television, a content receiver, a set-top box, a printer, a mobile handset, a smartphone, a personal digital assistant ("PDA"), a wireless receiver and/or transmitter, a base station, a communication management device, a router, a switch, a controller, an access point, and/or a client device.

FIG. 1B illustrates another example of a system 101 according to an embodiment. As illustrated in FIG. 1B, clean dialysate 114 is used for dialysis. Spent dialysate drains to a drain bag 120, via a drain line 116. In other embodiments, spend dialysate may drain to a fixed drain (e.g., toilet, sink, or other drain). As the spent dialysate drains, a light-permeable chamber 118 is configured to receive at least a portion of the spent dialysate. The light source 102 is configured to emit light through the light-permeable chamber 118, and the light sensor 108 is configured to sense the light emitted through the light-permeable chamber 118. The light sensor 108 is configured to transmit data to the dialysate analysis device 110. An example of a light-permeable chamber 118 is described below with respect to FIG. 6A. The light source 102 and light sensor 108 may be part of a light sensing device, such as the example light-sensing device 605 illustrated in FIG. 6B.

2. Analyzing Spent Dialysate in a Drain Bag 2.1 Apparatus

In an embodiment, an apparatus is provided that facilitates placement of a light sensor relative to spent dialysate in a drain bag. Specifically, the apparatus may help ensure that the light sensor and drain bag are positioned, relative to each other, in a configuration that helps ensure accurate and consistent light readings. In the following example, the light sensor is assumed to be part of a dialysate analysis device, such as a smartphone or tablet. In other examples (not shown), the light sensor may be physically separate from the dialysate analysis device and references below to a "device" or "dialysate analysis device" may refer to the light sensor only. In some examples described herein, the light sensor is integrated into the apparatus.

Figure 2A:
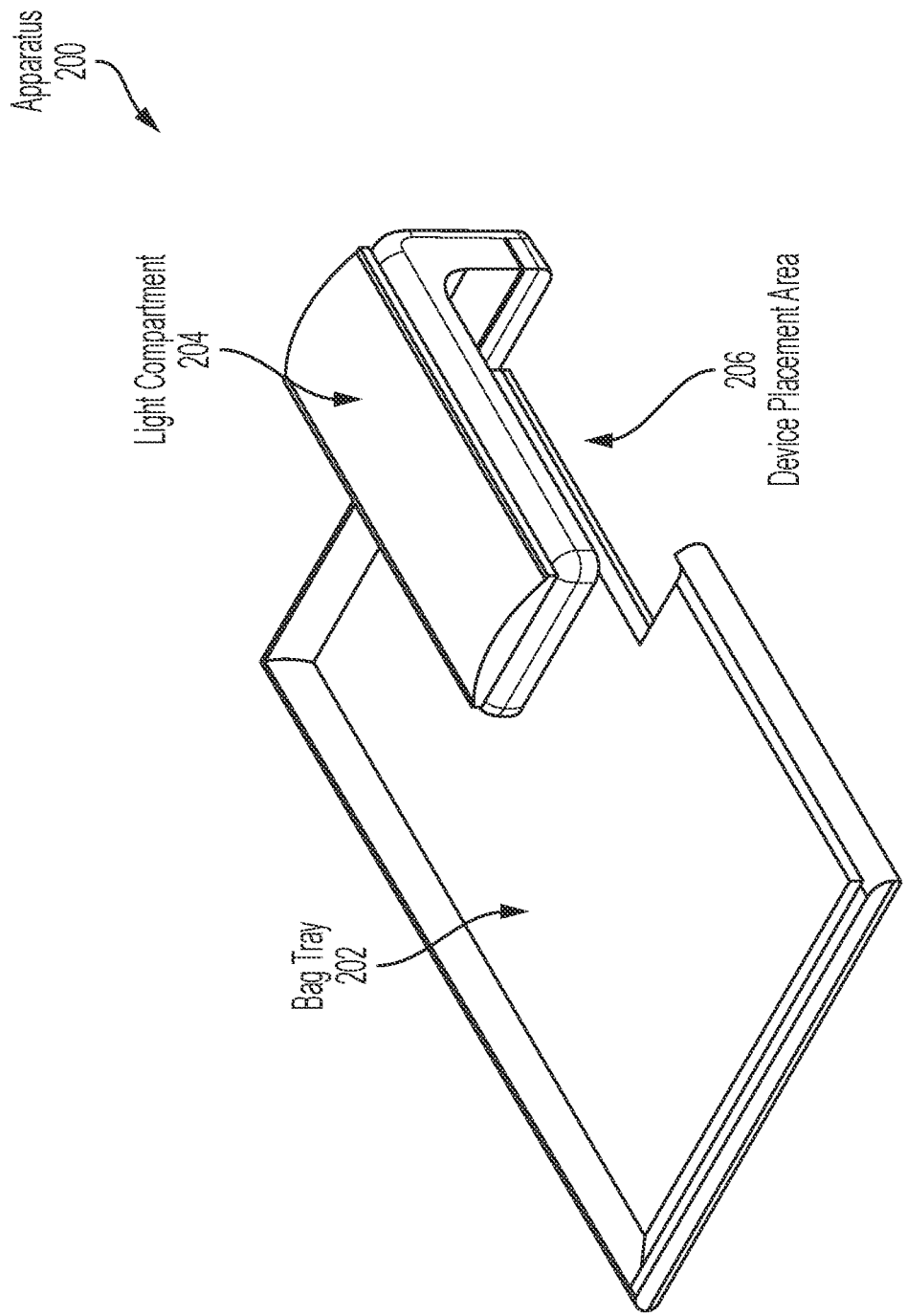
FIG. 2A is an illustration of a perspective view of an example of an apparatus according to an embodiment.

FIG. 2A is an illustration of a perspective view of an example of an apparatus 200 according to an embodiment. In this example, the apparatus 200 includes a bag tray 202 configured to receive at least part of a dialysis drain bag (not shown). Embodiments that help position a light sensor relative to a drain bag may be used in any dialysis setting where spent dialysate drains into a bag, versus a sink or other location. The bag tray 202 helps ensure consistent positioning of the drain bag during spent dialysate analysis. A device placement area 206 is defined by one or more surfaces (in this example, three surfaces that define a rectangular area) of the apparatus 200 that indicate the intended positioning of the dialysate analysis device. For example, as illustrated in FIG. 2A, the device placement area 206 helps ensure that the dialysate analysis device is positioned beneath a corner of the drain bag. In addition, the device placement area 206 may help ensure consistent positioning of the dialysate analysis device relative to a light source. For example, as illustrated in FIG. 2A, the device placement area 206 helps ensure that the dialysate analysis device is positioned below a light compartment 204 that houses one or more light sources as described in further detail below. The device placement area 206 may be sized to accommodate a particular type of dialysate analysis device (e.g., a special-purpose medical device). Alternatively, the device placement area 206 may be sized to accommodate multiple types of dialysate analysis devices (e.g., smartphones and/or tablets that may vary in size depending on make and model).

Figure 2B:
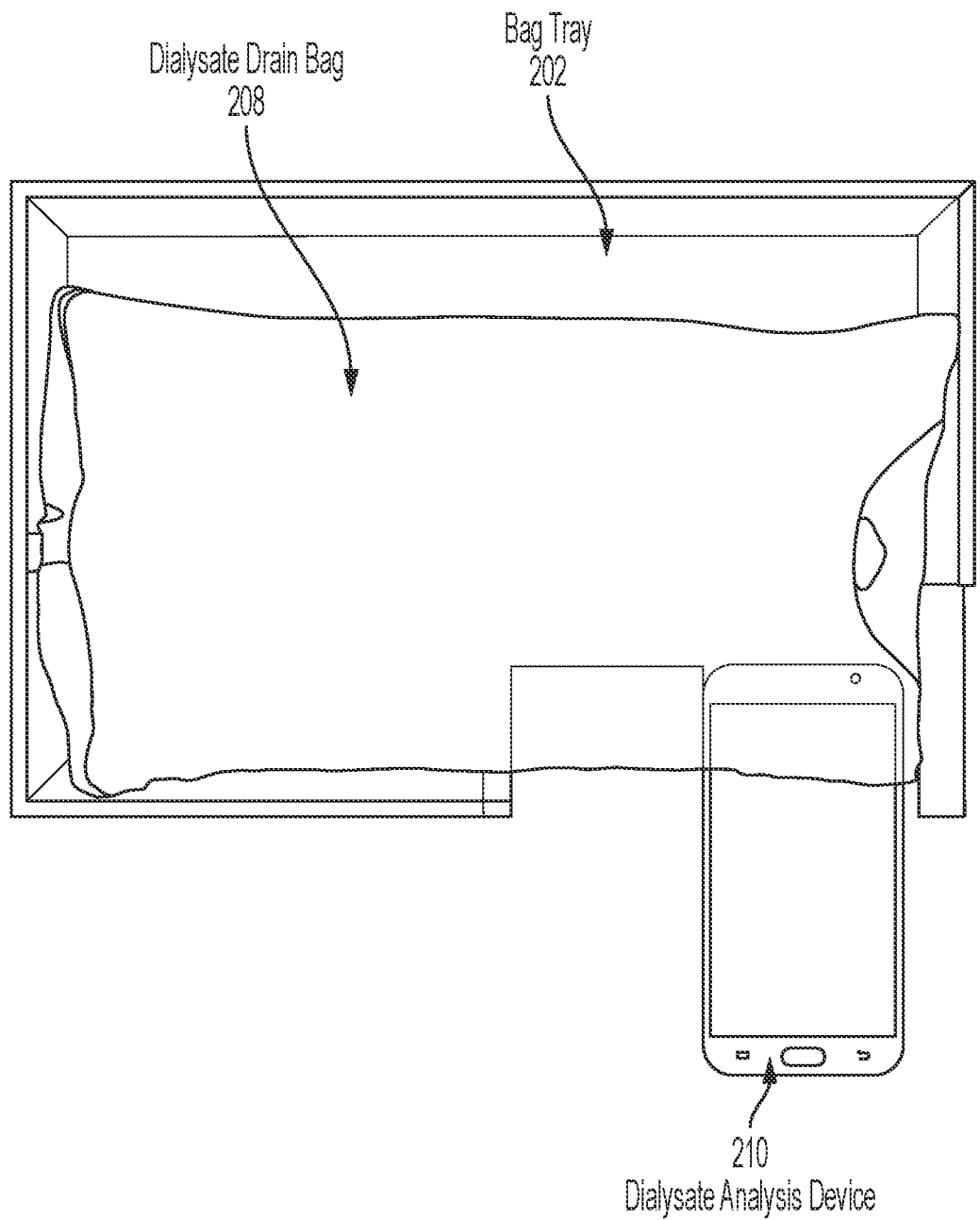
FIG. 2B is an illustration of a top-down view of the apparatus of FIG. 2A without a light compartment according to an embodiment.

FIG. 2B is an illustration of a top-down view of the apparatus 200 of FIG. 2A without a light compartment, according to an embodiment. Specifically, FIG. 2B illustrates placement of a dialysate drain bag 208 on the bag tray 202. In addition, FIG. 2B illustrates placement of a dialysate analysis device 210 (in this example, a smartphone with a light-sensing camera). In this example, the device placement area 206 helps ensure that the dialysate analysis device 210 is positioned under a corner of the dialysate drain bag 208. FIG. 2B further illustrates an example of a device placement area 206 that is large enough to accommodate multiple types of devices.

Figure 2C:
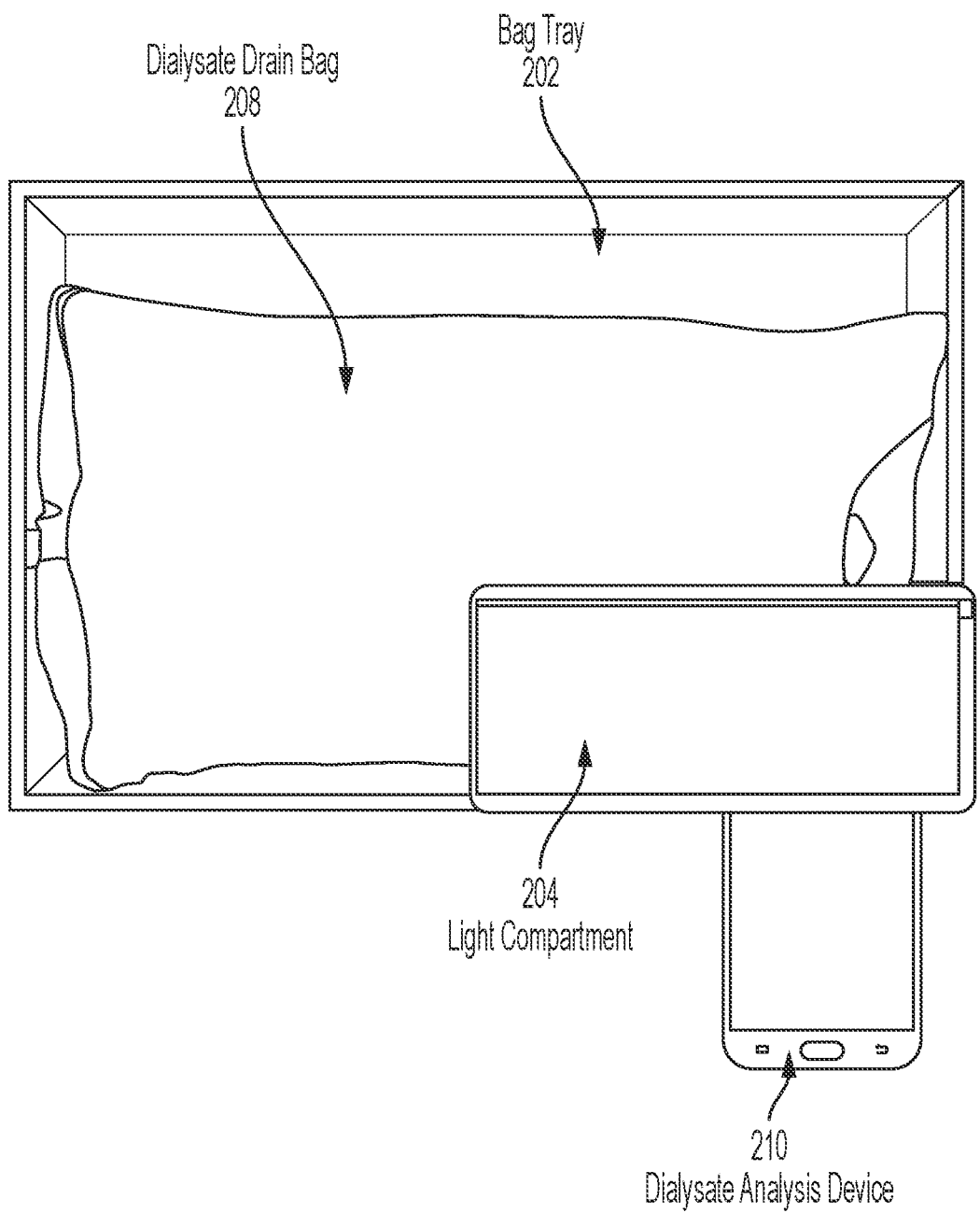
FIG. 2C is an illustration of a top-down view of the apparatus of FIG. 2A with a light compartment according to an embodiment.
Figure 2D:
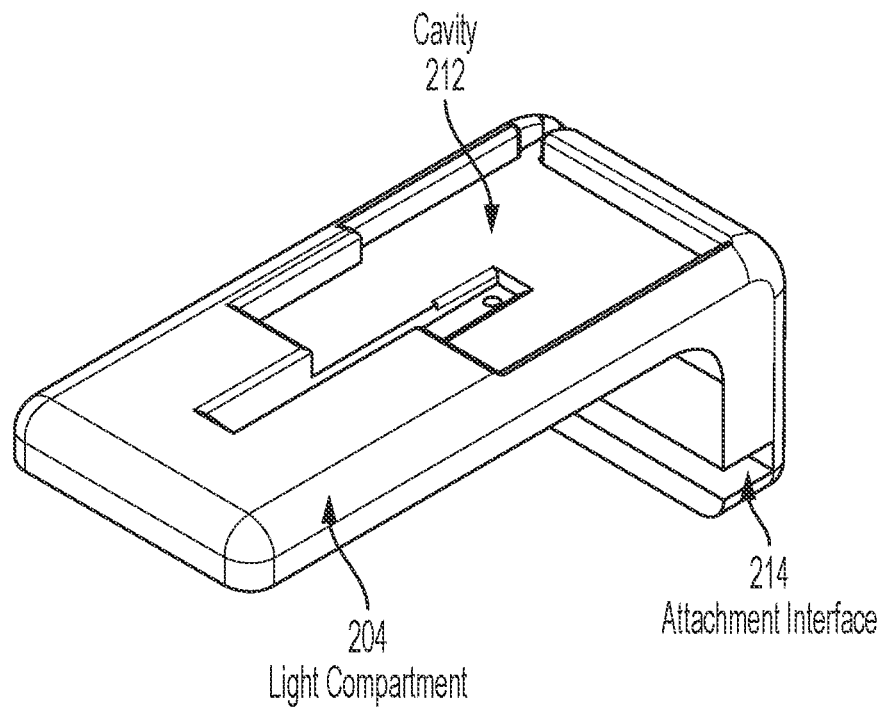
FIG. 2D is an illustration of a perspective view of an example of a light compartment for the apparatus of FIG. 2A according to an embodiment.
Figure 2E:
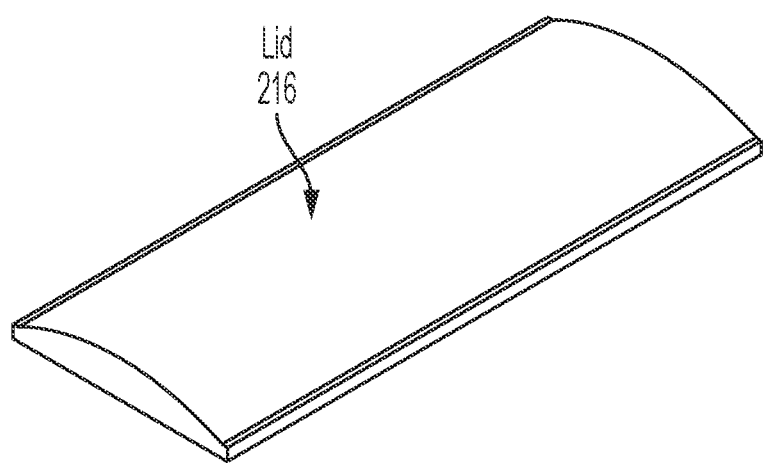
FIG. 2E is an illustration of a perspective view of an example of a lid for the light compartment of FIG. 2D according to an embodiment.

FIG. 2C is an illustration of a top-down view of the apparatus 200 of FIG. 2A with a light compartment 204 attached, according to an embodiment. As illustrated in FIG. 2C, the light compartment 204 is positioned above the dialysate analysis device 210, such that one or more light sources housed in the light compartment 204 emit(s) light toward or approximately toward a light sensor in the dialysate analysis device 210. The light compartment 204 may be a non-removable part of the apparatus 200. Alternatively, the light compartment 204 may be removable from the apparatus 200. For example, FIG. 2D is an illustration of a perspective view of an example of a light compartment 204 for the apparatus 200 of FIG. 2A, which includes an attachment interface 214 for attaching the light compartment 204 to the bag tray 202. The light compartment 204 includes a cavity 212 configured to house electrical components, including but not limited to a light source. FIG. 2E is an illustration of a perspective view of an example of a lid 216 for the light compartment 204 of FIG. 2D according to an embodiment. In this example, the lid 216 is removable, to provide access to the electrical components housed in the light compartment 204 (for example, to replace LED's and/or service other electrical components).

Figure 2F:
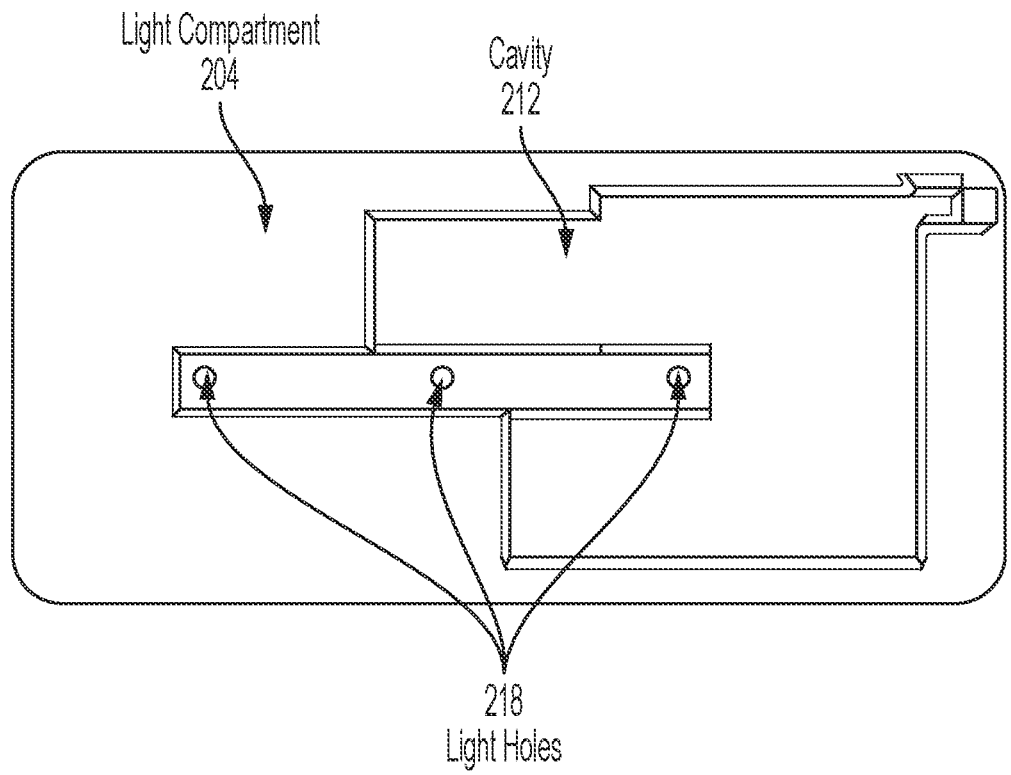
FIG. 2F is an illustration of a top-down view of the light compartment of FIG. 2D according to an embodiment.

FIG. 2F is an illustration of a top-down view of the light compartment 204 of FIG. 2D according to an embodiment. Specifically, FIG. 2F is an illustration of a top-down view of the light compartment 204 with the lid 216 removed and without any electrical components installed. As illustrated in FIG. 2F, the light compartment 204 includes one or more light holes 218 through which one or more light sources emit light. In this example, the light compartment 204 includes three light holes 218. The light holes 218 may be designed to accommodate light sources (e.g., lasers and/or LED's) that emit light at different respective wavelengths. For example, one of the light holes 218 may accommodate a light source that emits light at about 1300 nm; another of the light holes 218 may accommodate a light source that emits light at about 810 nm; and another of the light holes 218 may accommodate a light source that emits light at about 660 nm. In other examples (not shown), more or fewer light sources may be used. One or more light holes 218 may be positioned within the cavity 212, such that one or more electrical components cover one or more of the light holes 218 when installed.

Figure 2G:
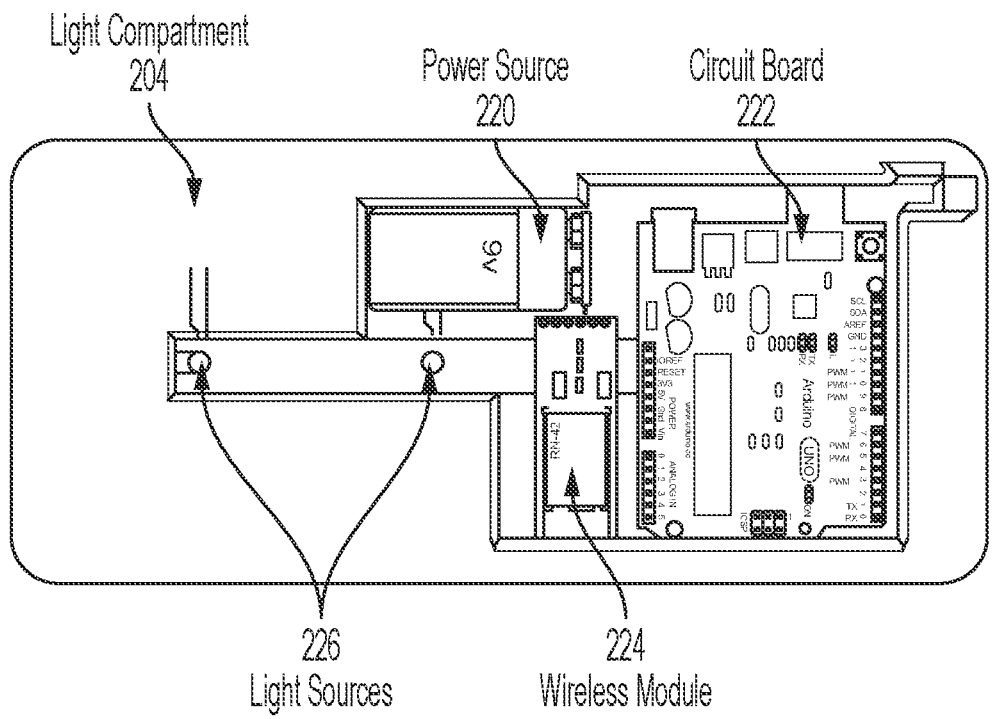
FIG. 2G is an illustration of a top-down view of an electrical component layout for the light compartment of FIG. 2D according to an embodiment.

FIG. 2G is an illustration of a top-down view of an electrical component layout for the light compartment 204 of FIG. 2D according to an embodiment. In this example, the electrical components are powered by a power source 220 (e.g., a battery and/or external power source such as an A/C adapter or USB cable). In the example illustrated in FIG. 2G, a 9-volt battery is used. In another example, the electrical components may include a rechargeable battery, so that the apparatus 200 can be disconnected from external power when the rechargeable battery is sufficiently charged. A circuit board 222 implements logic in hardware, firmware, and/or software to control operation of the electrical components. A wireless module 224 (e.g., a Bluetooth® and/or Wi-Fi module) is configured to transmit and receive data in communication with the dialysate analysis device 210. In this example, there are three light sources 226, one of them being concealed by a wireless module 224.

Figure 2H:
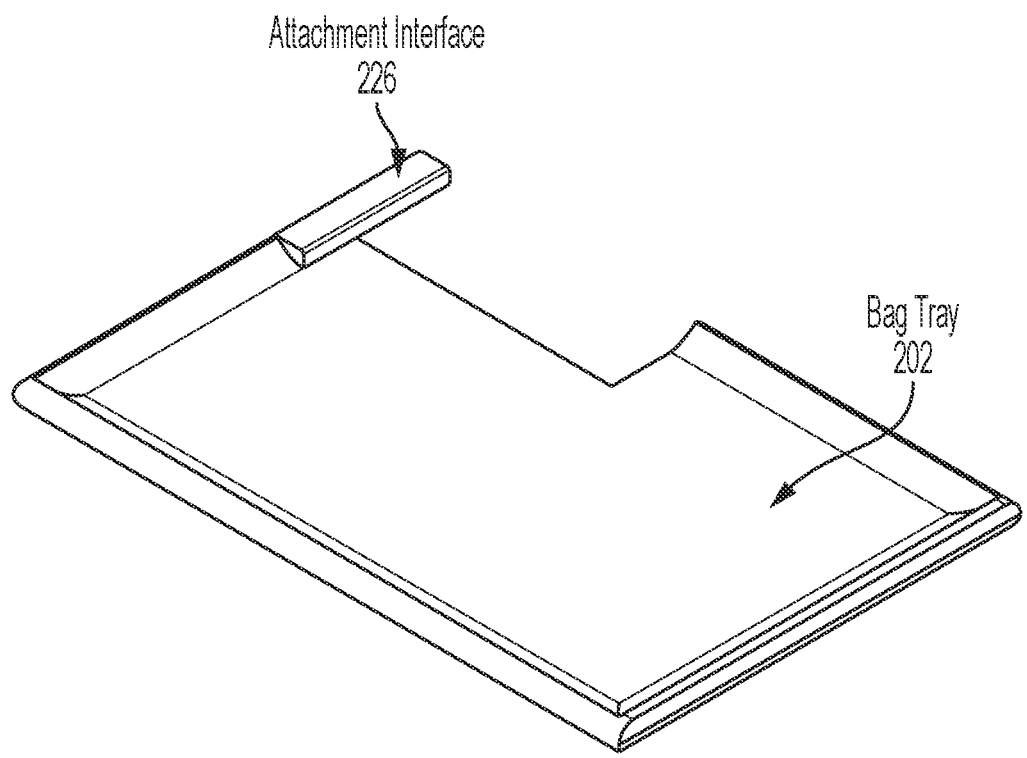
FIG. 2H is an illustration of another perspective view of the apparatus of FIG. 2A according to an embodiment.
Figure 21:
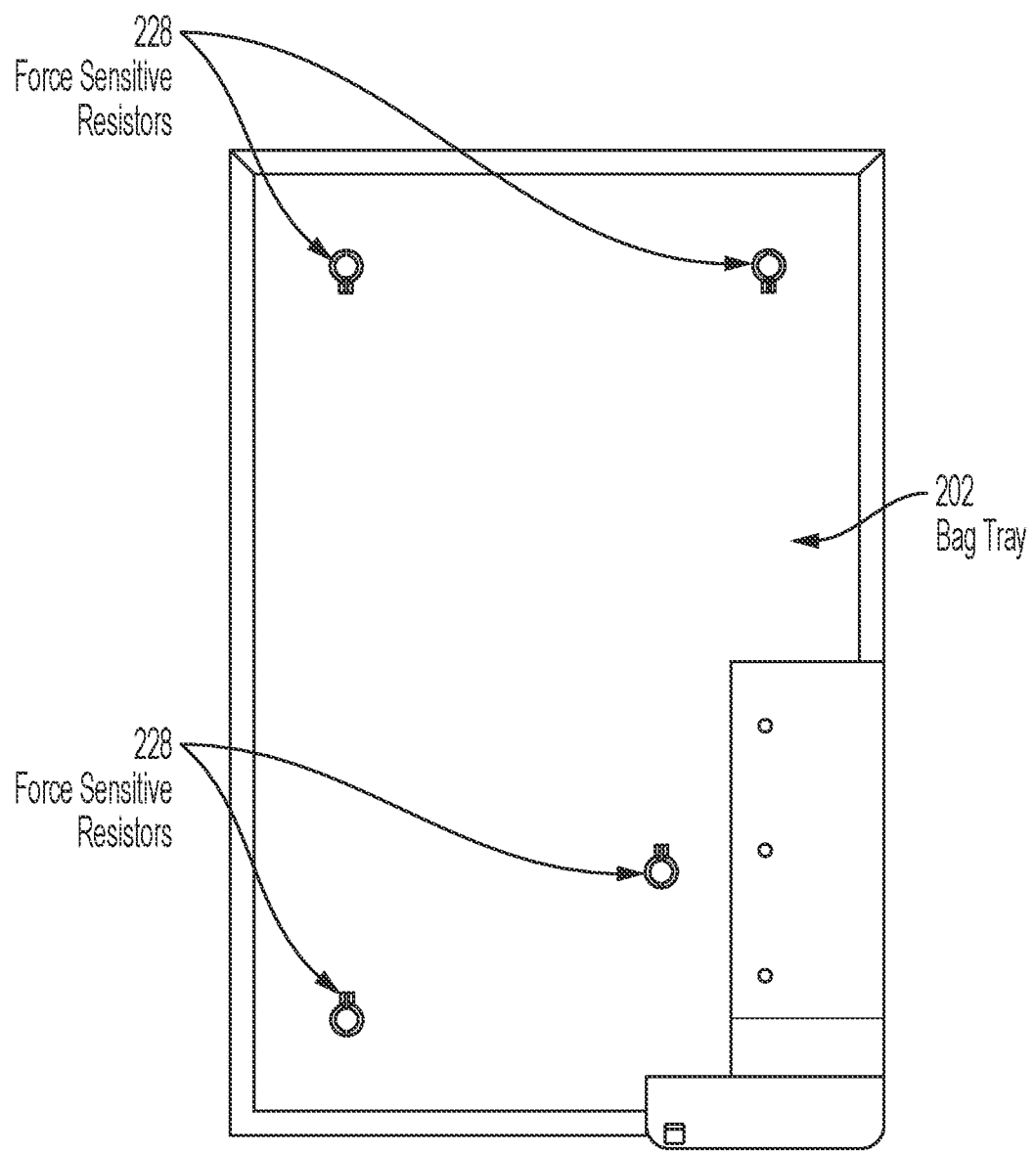

FIG. 2H is an illustration of another perspective view of the apparatus of FIG. 2A according to an embodiment. As illustrated in FIG. 2H, an attachment interface 226 is configured to receive the light compartment 204, for example by interfacing with the light compartment 204's attachment interface 214 illustrated in FIG. 2D.

In an embodiment, the apparatus 200 includes a scale configured to weigh the dialysate drain bag 208. For ease of discussion, as used herein, the terms "weigh" and "weight" may refer to measuring either the mass or weight of the dialysate drain bag 208, as those terms are defined in the art. For example, FIG. 2I is an illustration of a bottom-up view of the apparatus 200 of FIG. 2A according to an embodiment. As illustrated in FIG. 2I, one or more force sensitive resistors 228 is/are disposed in or along the bag tray 202. The force sensitive resistors 228 are configured to sense the weight of the dialysate drain bag 208. The force sensitive resistors 228 may be pre-tared, based on a known weight of the apparatus 200 and/or an empty dialysate drain bag 208. Alternatively, the force sensitive resistors 228 may require taring and/or other calibration when analyzing spent dialysate. Weighing the drain bag may be a requirement in some forms of peritoneal dialysis, and the apparatus 200 may help satisfy that requirement. In addition, the weight of the drain bag may be used to calibrate turbidity measurements. Specifically, a heavier drain bag may be assumed to be fuller and therefore physically deeper, and a lighter drain bag may be assumed to be emptier and therefore physically shallower. Turbidity calculations may be adjusted to account for the assumed depth of the drain bag, which may be based, for example, on average depth measurements taken in a laboratory setting and integrated into programming of the dialysate analysis device.

Figure 3A:
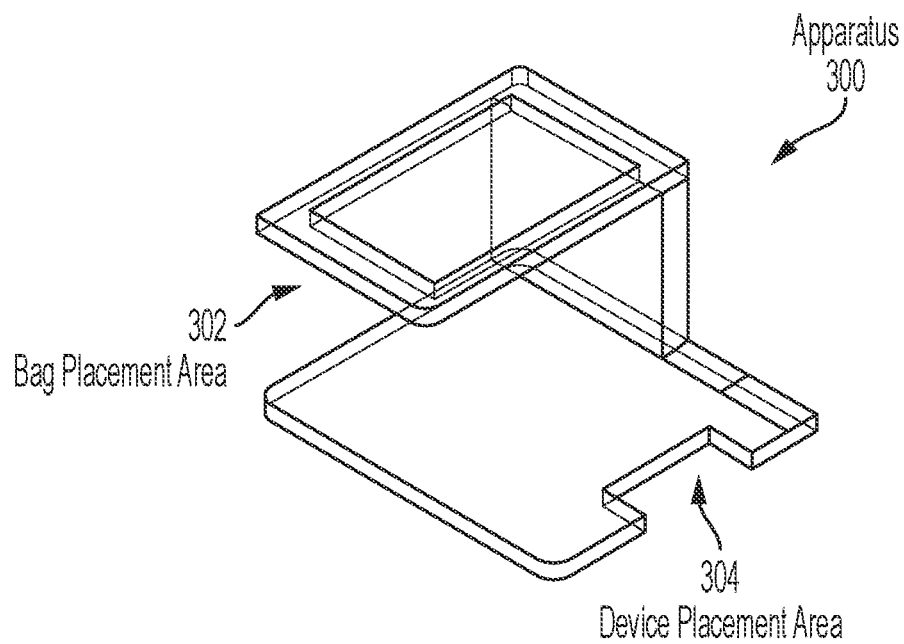
FIG. 3A is an illustration of a perspective view of another example of an apparatus according to an embodiment.

FIG. 3A is an illustration of a perspective view of another example of an apparatus 300 according to an embodiment. In this example, the apparatus 300 does not include a light compartment, and a bag placement area 302 does not include a bag tray. The apparatus 300 may be formed of clear plastic to increase visibility and reduce shadows that might otherwise interfere with ambient light readings. In addition, the upper portion of the apparatus 300 may be positioned high enough, i.e., have sufficient clearance above the drain bag, to reduce shadows that might otherwise be cast on the dialysate analysis device's light sensor(s).

Figure 3B:
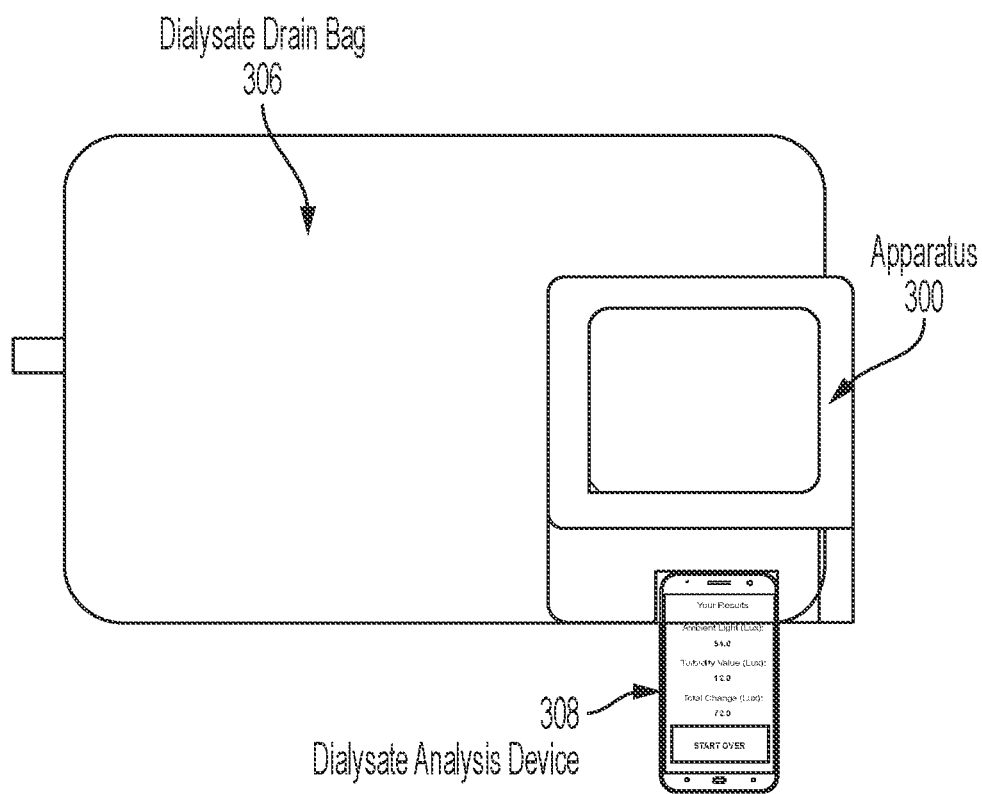
FIG. 3B is an illustration of a top-down view of the apparatus of FIG. 3A according to an embodiment.

As in the example of FIGS. 2A-2I, a device placement area 304 is defined by one or more surfaces (in this example, three surfaces that define a rectangular area) of the apparatus 300 that indicate the intended positioning of the dialysate analysis device. In addition, the bag placement area 302 helps ensure consistent positioning of the drain bag during spent dialysate analysis. For example, FIG. 3B is an illustration of a top-down view of the apparatus 300 of FIG. 3A according to an embodiment, in which the apparatus 300 helps ensure consistent positioning of a dialysate drain bag 306 relative to a dialysate analysis device 308. The apparatus 300 of FIGS. 3A-3B has fewer features than the apparatus 200 of FIGS. 2A-2I, but may be more portable and/or less expensive. In an embodiment, a dialysate analysis device is configured to be compatible with two or more different types of apparatus, for example via a hardware switch and/or a setting in a software application.

Figure 12A:
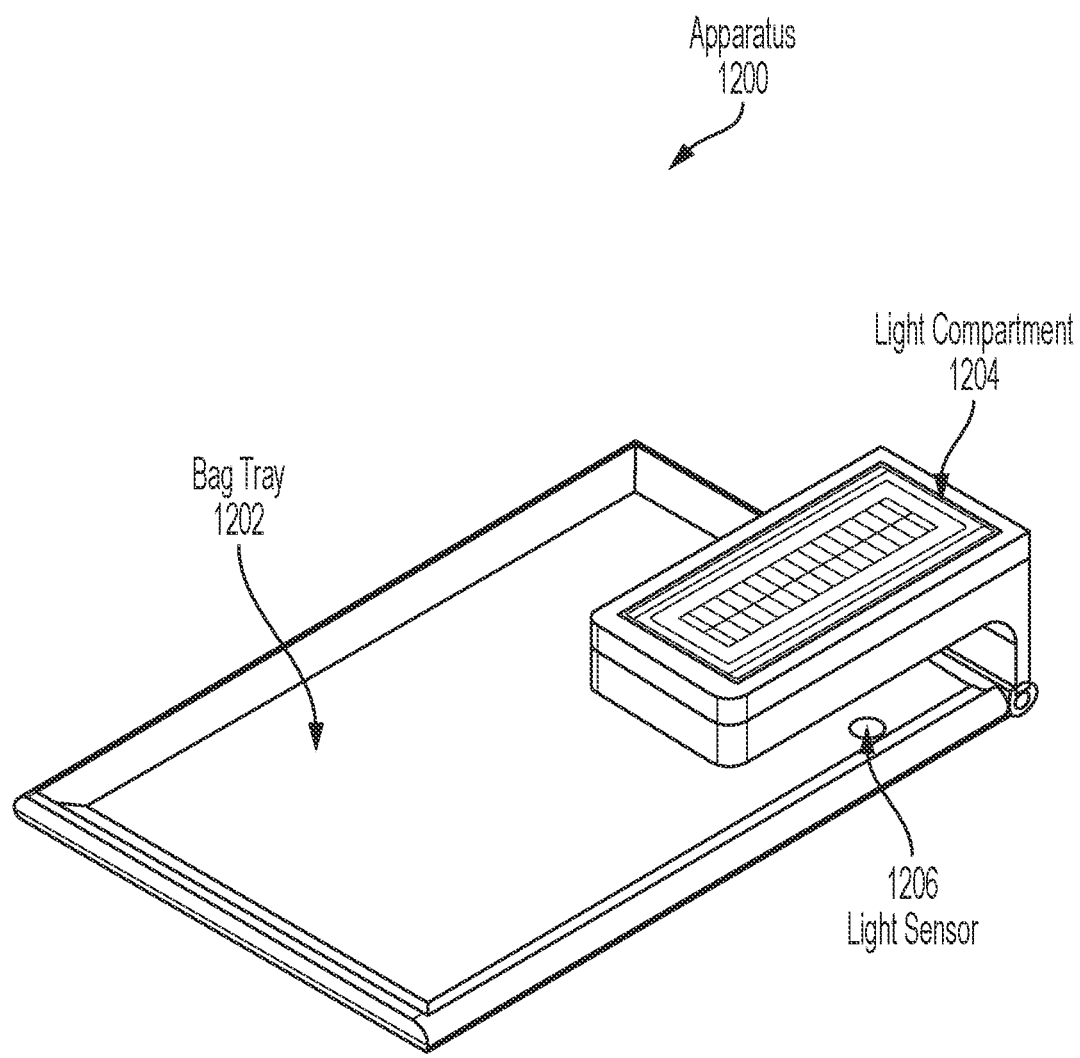
FIG. 12A is an illustration of a perspective view of another example of an apparatus according to an embodiment.

FIG. 12A is an illustration of a perspective view of another example of an apparatus 1200 according to an embodiment. In general, the apparatus 1200 may include one or more features described above with respect to the example of FIGS. 2A-2I, such as a bag tray 1202. However, in this example, a light sensor 1206 is integrated into the apparatus 1200 and disposed so as to sense light emitted by a light compartment 1204 also integrated into the apparatus 1200. The apparatus 1200 may also include hardware, firmware, and/or software configured to perform one or more operations for dialysate analysis, as described herein (e.g., one or more operations described above as being performed by a dialysate analysis device). This example does not include a physically separate dialysate analysis device; dialysate analysis is performed by the apparatus itself. Alternatively, the apparatus 1200 may also be configured to accommodate a separate dialysate analysis device, which may be configured to perform at least some of the dialysate analysis operations.

Figure 12B:
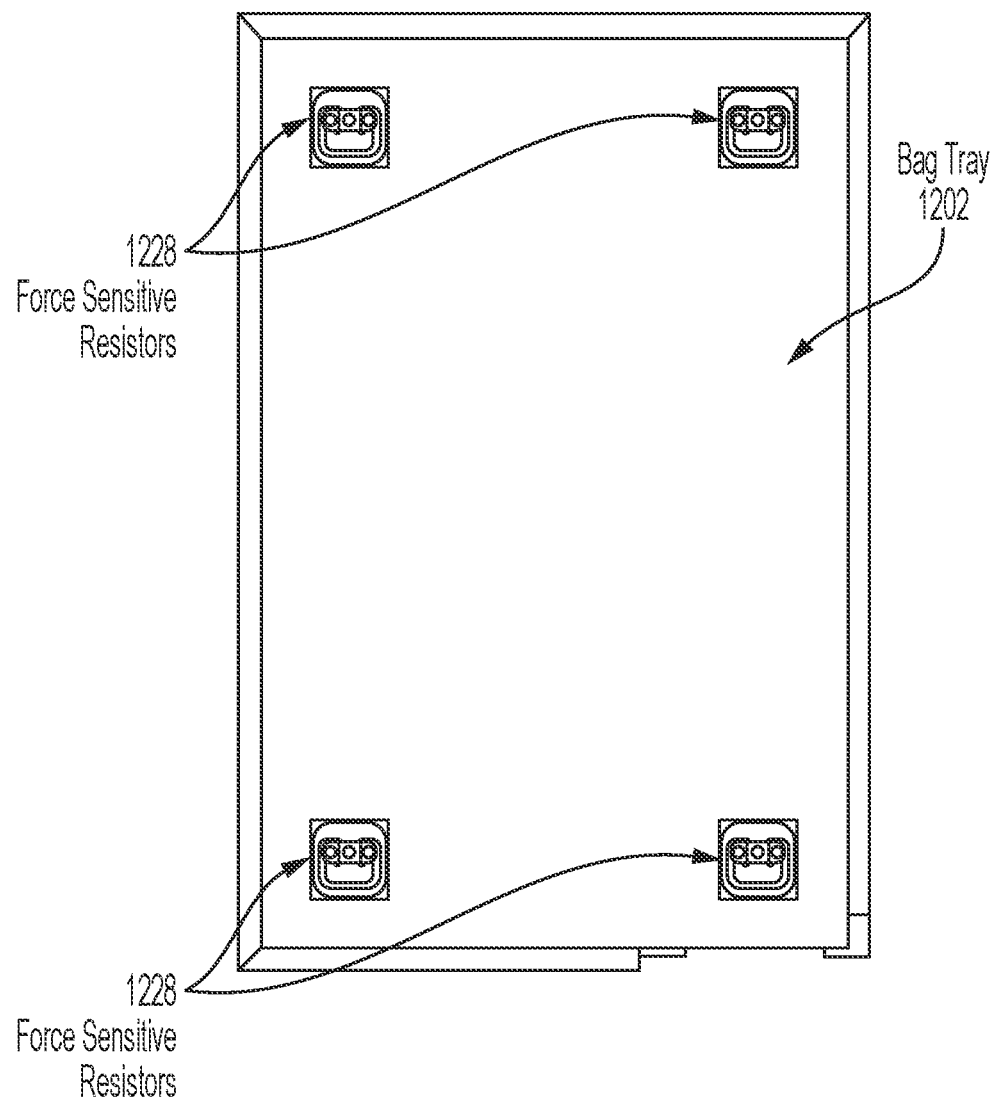
FIG. 12B is an illustration of a bottom-up view of the apparatus of FIG. 12A according to an embodiment.

In an embodiment, the apparatus 1200 includes a monochromator (not shown). A monochromator may be used, for example, to ensure that a light-emitting component disposed in the light compartment 1204 emits a narrow wavelength or radiation, to help improve the accuracy of light readings and subsequent analysis. Alternatively or additionally, the apparatus 1200 may include a cover and/or enclosure (not shown) that fully or partially surrounds the apparatus 1200 (e.g., fully or partially surrounding the light compartment 1204 and/or light sensor 1206), to reduce ambient light (e.g., creating an environment akin to a dark room), for improved detection of light emitted from the light compartment 1204. FIG. 12B is an illustration of a bottom-up view of the apparatus 1200 of FIG. 12A according to an embodiment. As illustrated in FIG. 12B, the apparatus 1200 may include force-sensitive resistors 1228 integrated into an underside of the bag tray 1202. The force-sensitive resistors 1228 are configured to sense the weight of the dialysate drain bag. The force-sensitive resistors 1228 may be pre-tared, based on a known weight of the apparatus 1200 and/or an empty dialysate drain bag. Alternatively, the force-sensitive resistors 1228 may require taring and/or other calibration when analyzing spent dialysate. Weighing the drain bag may be a requirement in some forms of peritoneal dialysis, and the apparatus 1200 may help satisfy that requirement. In addition, the weight of the drain bag may be used to calibrate turbidity measurements. Specifically, a heavier drain bag may be assumed to be fuller and therefore physically deeper, and a lighter drain bag may be assumed to be emptier and therefore physically shallower. Turbidity calculations may be adjusted to account for the assumed depth of the drain bag, which may be based, for example, on average depth measurements taken in a laboratory setting and integrated into programming of the dialysate analysis device.

Figure 12C:
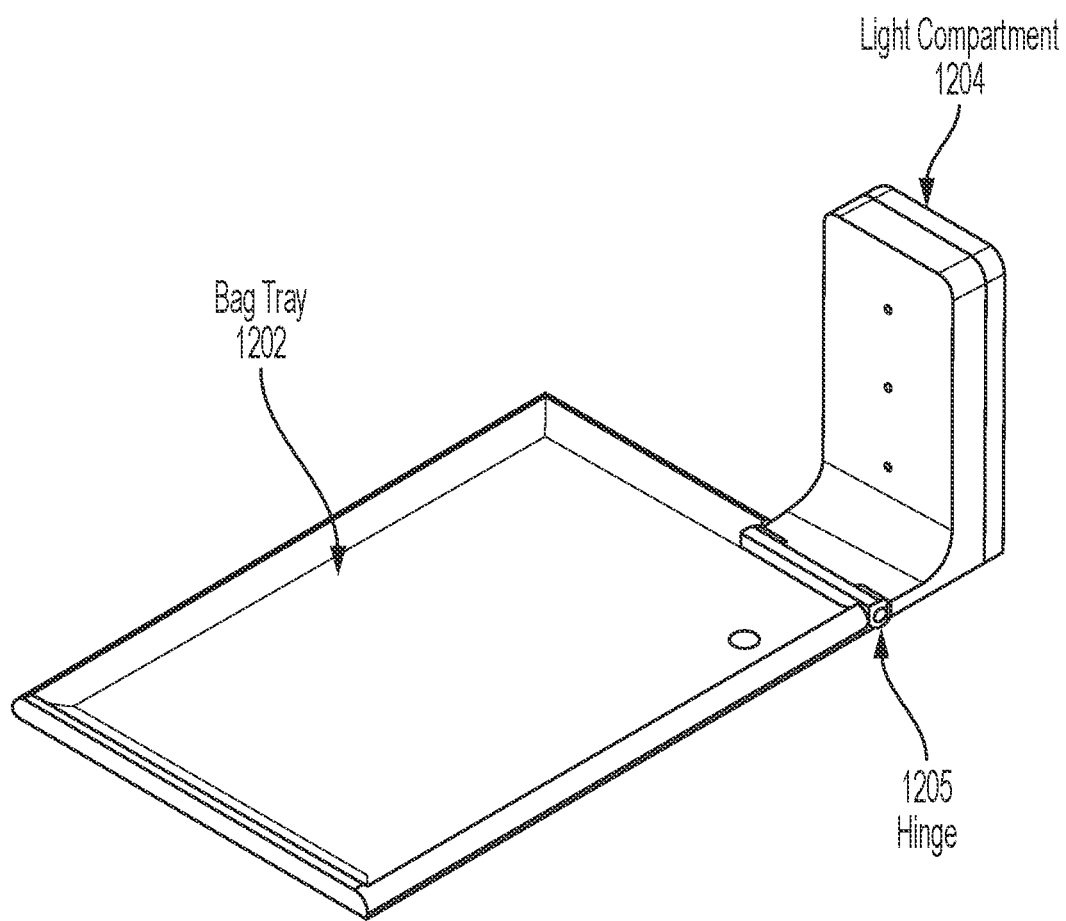
FIG. 12C is an illustration of a light compartment for the apparatus of FIG. 12A according to an embodiment.

FIG. 12C is an illustration of a light compartment 1204 for the apparatus of FIG. 12A according to an embodiment. The light compartment 1204 is positioned above the light sensor 1206, such that one or more light sources housed in the light compartment 1204 emit(s) light toward or approximately toward the light sensor 1206. The light compartment 1204 may be a non-removable part of the apparatus 1200. Alternatively, the light compartment 1204 may be removable from the apparatus 1200.

As illustrated in FIG. 12C, the light compartment 1204 may be attached to the apparatus 1200 by a hinge 1205. The hinge 1205 may be a manual hinge or an automated hinge (e.g., using a motor under control of hardware, firmware, and/or software included in the apparatus 1200). The hinge 1205 allows for the light compartment 1204 to swivel upward, to facilitate placement of a drain bag on the bag tray 1202. The hinge 1205 may thus reduce the incidence of misplaced drain bags, providing a corresponding increase in the accuracy and utility of data gathered by the apparatus.

Figure 12D:
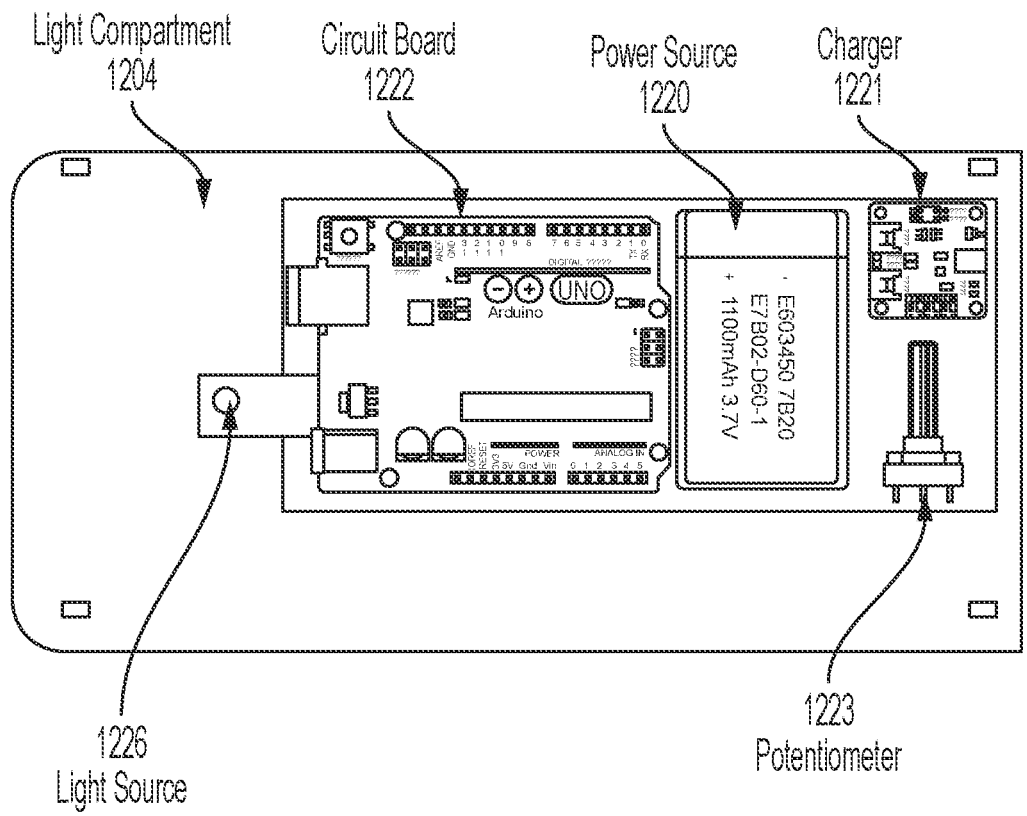
FIG. 12D is an illustration of an electrical component layout for the light compartment of FIG. 12C according to an embodiment.

FIG. 12D is an illustration of an electrical component layout for the light compartment 1204 of FIG. 12C according to an embodiment. In this example, the electrical components are powered by a power source 1220 (e.g., a battery and/or external power source such as an A/C adapter or USB cable). In the example illustrated in FIG. 12D, a rechargeable battery is used. The power source 1220 is rechargeable via a charger 1221. The apparatus 1200 may be disconnected from external power when the power source 1220 is sufficiently charged. In another example, the electrical components may include a non-rechargeable power source, such as a 9-volt battery or other kind of non-rechargeable power source.

A circuit board 1222 implements logic in hardware, firmware, and/or software to control operation of the electrical components. In an embodiment, the circuit board 1222 includes one or more processors configured to execute instructions to perform operations described herein. The apparatus 1200 may include one or more computer-readable media (not shown) storing such instructions. A wireless module (not shown) (e.g., a Bluetooth® and/or Wi-Fi module) is configured to transmit and receive data in communication with one or more other components (e.g., a dialysis system and/or server as described herein). In this example, there are three light sources 1226, two of them being concealed by the circuit board 1222. A potentiometer 1223 may be included, for example, for use with an integrated display as described below.

Figure 12E:
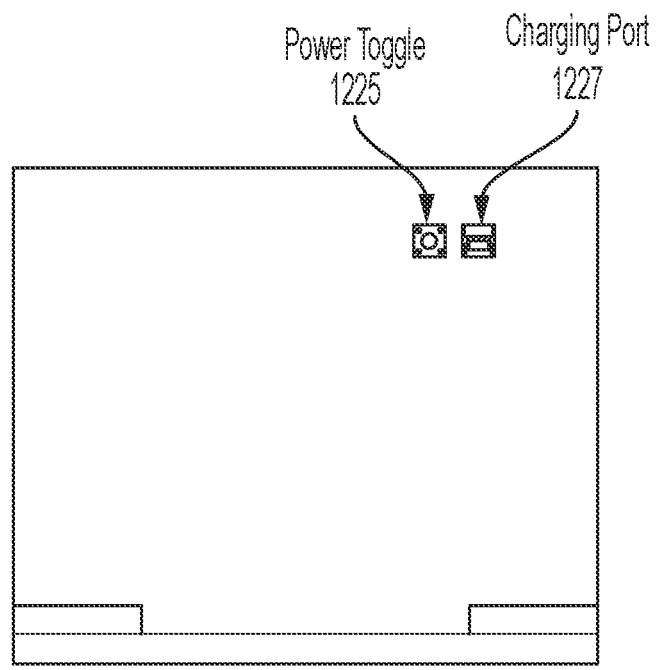
FIG. 12E is an illustration of an end view of the light compartment of FIG. 12C according to an embodiment.

FIG. 12E is an illustration of an end view of the light compartment 1204 of FIG. 12C according to an embodiment. A power toggle 1225 (e.g., a button, switch, or other kind of toggle) allows for manual control of power to the apparatus 1200. A charging port 1227 is configured to receive a charging cable (e.g., a USB charging cable, AC adapter, or other kind of charging cable) to charge the power source 1220.

Figure 12F:
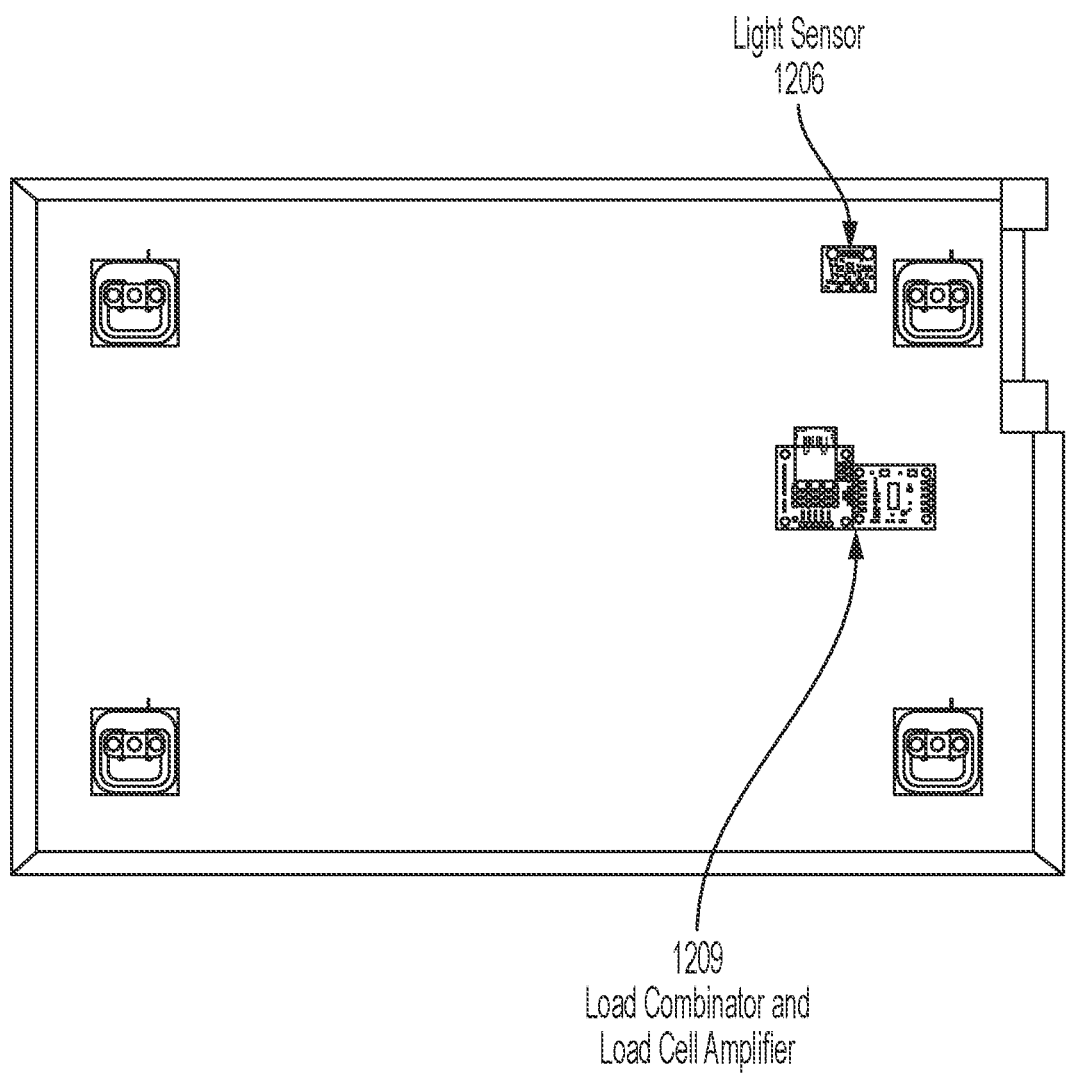
FIG. 12F is another illustration of a bottom-up view of the apparatus of FIG. 12 according to an embodiment.

FIG. 12F is another illustration of a bottom-up view of the apparatus 1200 of FIG. 12 according to an embodiment. Specifically, FIG. 12F illustrates the location of the light sensor 1206 from this perspective. FIG. 12F further illustrates the location of a load combinator and load cell amplifier 1209 from this perspective. In an embodiment, placing the load combinator and load cell amplifier 1209 near the hinge of the light compartment 1204 helps ensure that electronic hardware is located near the circuits included in the light sensor enclosure.

Figure 12G:
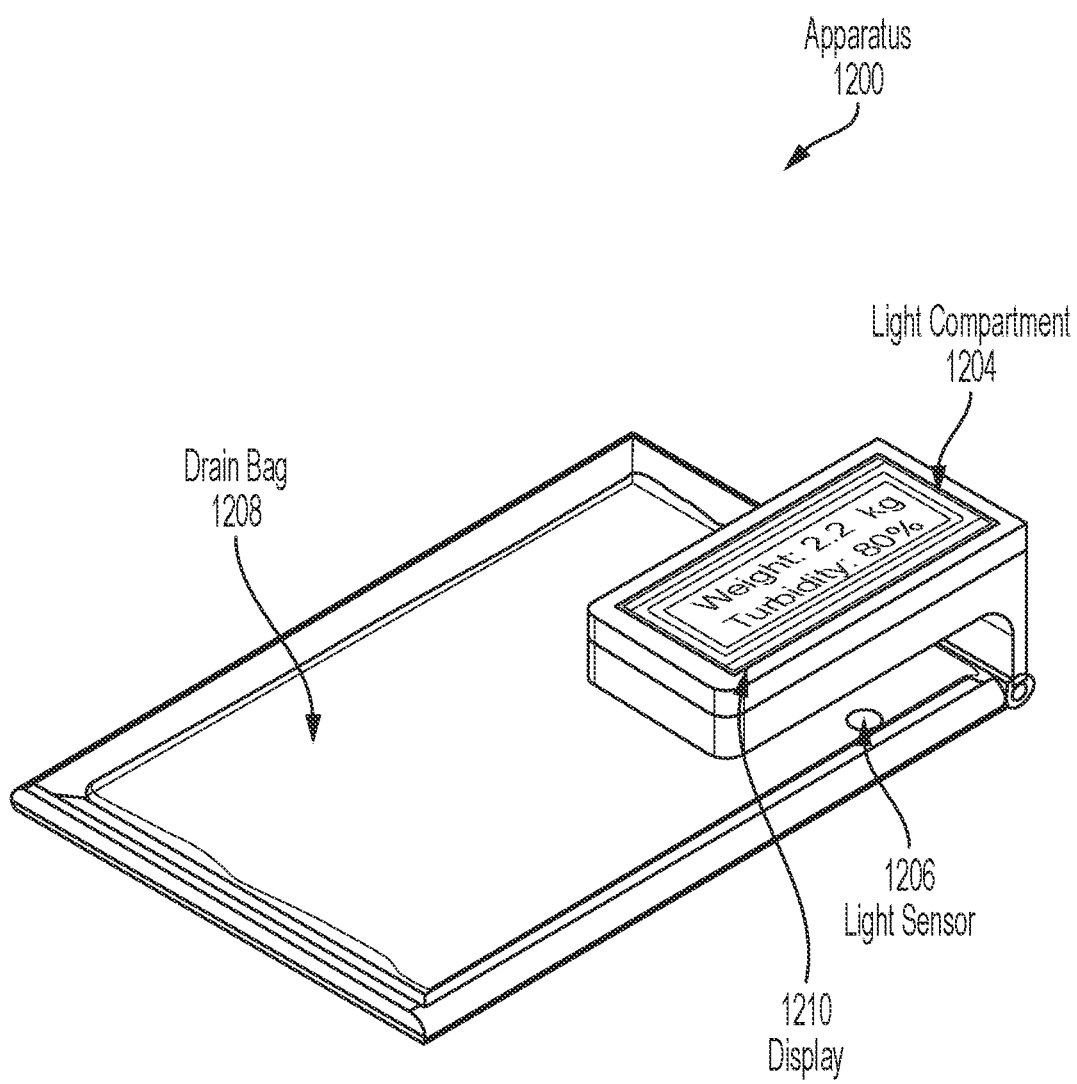
FIG. 12G is an illustration of a perspective view of an example of using the apparatus of FIG. 12A according to an embodiment.

FIG. 12G is an illustration of a perspective view of an example of using the apparatus 1200 of FIG. 12A according to an embodiment. As illustrated in FIG. 12G, when the apparatus 1200 is in use, a drain bag 1208 is positioned so that light emitted by the light compartment 1204 passes through the drain bag 1208. The light sensor 1206 detects the light. Hardware, firmware, and/or software disposed in the apparatus 1200 is configured to analyze spent dialysate in the drain bag 1208, based at least on the light sensed by the light sensor 1206. Some examples of operations for analyzing spent dialysate are described herein. In this example, the apparatus 1200 also weighs the drain bag 1208, using the force sensitive resistors 1228 integrated into an underside of the bag tray 1202 (described above). The apparatus 1200 is configured to display results of analyzing the spent dialysate on a digital display 1210. The results may include weight and turbidity, as illustrated in FIG. 12G, and/or other results of analyzing data gathered by the apparatus 1200. In general, the digital display 1210 may be configured to display one or more user interface elements, for example as described with respect to FIGS. 8A-8E herein, with appropriate modifications to accommodate the size and type of the digital display 1210. The digital display 1210 may be a display only, or may be a touch screen or other kind of display configured to receive user input. Alternatively or additionally, the apparatus 1200 may include one or more other user input mechanisms, such as a microphone, buttons, video camera, and/or another kind of input mechanism allowing the apparatus 1200 to receive user input and control operation of the apparatus 1200.

In some examples (not shown), an apparatus as described herein may be integrated with a hook scale. The hook scale may be used to weigh the dialysate drain bag, as an alternative or in addition to force sensitive resistors integrated in the apparatus. The apparatus may be configured to clamp onto the drain bag while it is hanging from a hook scale. Alternatively, the apparatus itself may include an integrated hook scale. A light source and light sensor may be positioned so that analyzing spent dialysate can be performed while the drain bag hangs from the separate or integrated hook scale. For example, the light source and light sensor may be disposed on opposing faces of a clamp that fastens to the drain bag while it is hanging from a separate or integrated hook scale. For example, apparatus 1200 may be configured such that hinge 1206 is spring loaded, causing rotation of light compartment 1204 toward bag tray 1202, which may enable clamping of the apparatus 1200 to a drain bag. For such an embodiment, bag tray 1202 may be reduced in size to generally correspond to the profile of light compartment 1204.

In an embodiment, an apparatus as described herein is configured so that the light compartment and light sensor are disposed on opposing faces of a clamp that fastens to a drain line. For example, apparatus 1200 may be configured such that hinge 1206 is spring loaded, causing rotation of the light compartment 1204 toward the light sensor 1206 disposed in an opposing surface of the apparatus 1200, which may enable clamping of the apparatus 1200 to a drain line (e.g., at a clear section of the drain line or a light-permeable chamber). In such examples, the term "predetermined position" may refer to a suitable alignment of the drain line with the light compartment 1204 and light sensor 1206. For such an embodiment, bag tray 1202 may be omitted. FIG. 6B, discussed above, shows an example of a clamping mechanism configured to clamp to a drain line; in an embodiment, the apparatus has a form factor similar to that shown in FIG. 6B.

The examples above describe apparatuses that, among other features, help ensure consistent positioning of a dialysate drain bag. The dialysis drain bag itself may be designed to provide positioning guidance. For example, the drain bag may include one or more lines, a ruler, and/or other marking(s) that indicate(s) the intended position of the drain bag on a drain bag tray. Such markings may be designed to align with corresponding markings on the drain bag tray. The relative transparency of the drain bag may allow the patient or other human operator to use the marking(s) to position the drain bag in a relatively consistent location. In light of the present disclosure, many different types of apparatus and/or other guiding features may be envisioned that help ensure consistent positioning of a dialysate drain bag.

2.2 Method

Figure 4:
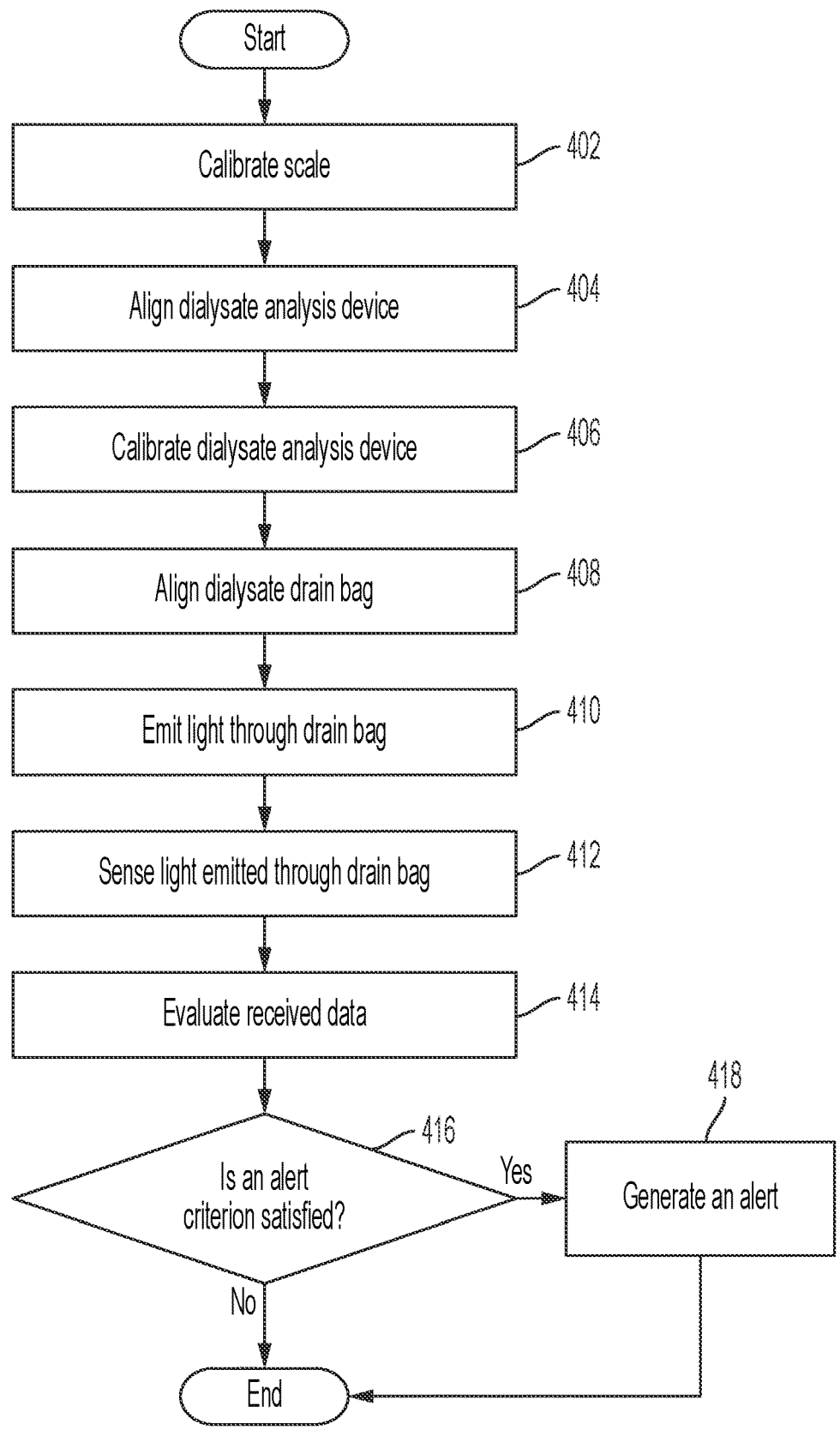
FIG. 4 is a flow diagram of an example of operations for analyzing spent dialysate in a drain bag according to an embodiment.

FIG. 4 is a flow diagram of an example of operations for analyzing spent dialysate in a drain bag according to an embodiment. One or more operations illustrated in FIG. 4 may be modified, rearranged, or omitted all together. Accordingly, the particular sequence of operations illustrated in FIG. 4 should not be construed as limiting the scope of one or more embodiments.

The operations described below include embodiments where dialysate analysis features are included in a dialysate analysis device physically separate from the apparatus on which the drain bag is placed. In embodiments where dialysate analysis features are integrated into the apparatus itself (for example, as in the example of FIGS. 12A-12G), operations described below with respect to the dialysate analysis device (e.g., calibration, analysis, etc.) may instead apply to hardware, firmware, and/or software integrated in the apparatus. In such examples, operations that rely on the dialysate analysis device being a physically separate component (e.g., positioning the device relative to the apparatus) may not be required. In other examples, some dialysate analysis features are integrated in the apparatus and others are performed by a separate dialysate analysis device.

The operations described below refer generally to embodiments using a drain bag. As described herein, other embodiments may use a drain line, for example by clamping to a drain line. Accordingly, where appropriate, references in this section to a drain bag may apply, mutatis mutandis, to a drain line.

In an embodiment, spent dialysate analysis is performed using an apparatus (e.g., the example apparatus of FIGS. 2A-2I) that includes a scale for weighing spent dialysate. The scale may require calibration (Operation 402) prior to use. For example, calibrating the scale may include taring the scale to disregard the weight of the apparatus and/or an empty drain bag. Calibrating the scale may be based on a bag containing clean dialysate, the weight of which may be compared with the weight of a drain bag containing spent dialysate.

In an embodiment, a dialysate analysis device is aligned with the apparatus (Operation 404). Specifically, the dialysate analysis device may be placed in a particular position indicated by a physical configuration of the apparatus (for example, the device placement area 206 of the example apparatus 200 illustrated in FIGS. 2A-2I, or the device placement area 304 of the apparatus 300 illustrated in FIGS. 3A-3B). In addition, audio and/or visual cues supplied by the apparatus and/or the dialysate analysis device may assist in aligning the dialysate analysis device with the apparatus. For example, the dialysate analysis device may supply audio and/or visual cues based on data from a proximity sensor and/or gyroscope, to assist a patient or other human operator in aligning the dialysate analysis device with the apparatus. Audio and/or visual cues may be presented in a graphical user interface, such as the example graphical user interface illustrated in FIGS. 5A-5I.

In an embodiment, the dialysate analysis device is calibrated (Operation 406). Calibrating the dialysate analysis device may involve taking one or more light readings, using a light sensor, when the drain bag containing spent dialysate is not present. Calibrating the dialysate analysis device may thus provide a baseline light reading for comparison with a light reading taken when the drain bag containing spent dialysate is present. For example, the baseline may be based on a historical average of readings. Alternatively or additionally, a baseline may be based on data (e.g., an average or mean) of readings taken from multiple non-peritonitis drain bags, in a laboratory setting and/or in practice.

In an embodiment, the drain bag containing spent dialysate is aligned with the apparatus (Operation 408). Specifically, the drain bag may be placed in a particular position indicated by a physical configuration of the apparatus (for example, the bag tray 202 of the example apparatus 200 illustrated in FIGS. 2A-2I, the bag placement area 302 of the apparatus 300 illustrated in FIGS. 3A-3B, or the bag tray 1202 of the example apparatus 1200 illustrated in FIGS. 12A-12G). In addition, audio and/or visual cues supplied by the apparatus and/or the dialysate analysis device may assist in aligning the drain bag with the apparatus. For example, the dialysate analysis device may supply audio and/or visual cues based on data from a scale (e.g., one or more force sensitive resistors 228 as illustrated in FIG. 2I, or one or more force sensitive resistors 1228 as illustrated in FIG. 12B), to assist a patient or other human operator in aligning the drain bag with the apparatus. Audio and/or visual cues may be presented in a graphical user interface, such as the example graphical user interface illustrated in FIGS. 5A-5I, and/or on a digital display integrated into the apparatus as illustrated in FIG. 12G.

In an embodiment, light is emitted through the drain bag (Operation 410). The light emitted through the drain bag may be ambient light (e.g., from sunlight and/or one or more general-purpose lamps) in the environment. Alternatively, a dedicated light source may emit light through the drain bag (for example, one or more light sources 226 of an apparatus 200 as illustrated in FIG. 2G). As discussed above, a dedicated light source may emit light responsive to an electrical signal or other type of instruction transmitted by the dialysate analysis device.

In an embodiment, a light sensor senses light emitted through the drain bag (Operation 412). Specifically, the light sensor senses light emitted at one or more particular wavelengths of interest for analyzing the spent dialysate. As discussed above, the light sensor may sense the light responsive to an electrical signal or other type of instruction transmitted by the dialysate analysis device. The light sensor may sense the light in a single reading. Alternatively, the light sensor may take multiple readings. When evaluating data received from the light sensor as described below, the dialysate analysis device may determine an average, mean, or other statistic based on multiple readings. In addition, the dialysate analysis device may discard outliers that deviate significantly from an average, mean, or other reference value. The light sensor may output a light reading (e.g., relative luminosity).

Figure 11A:
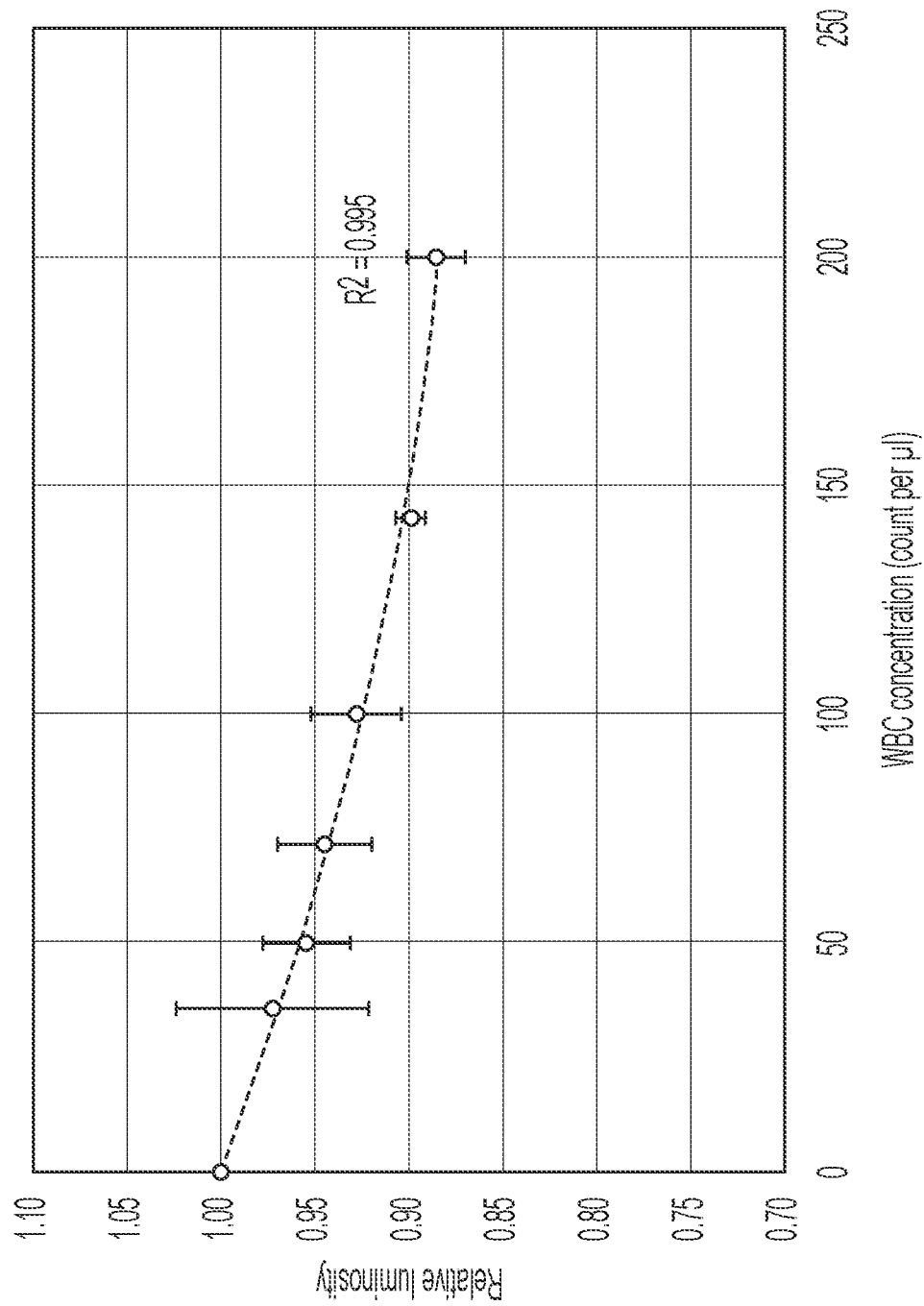
FIG. 11A shows a chart of test results demonstrating a correlation between relative luminosity and white blood cell concentration.
Figure 11B:
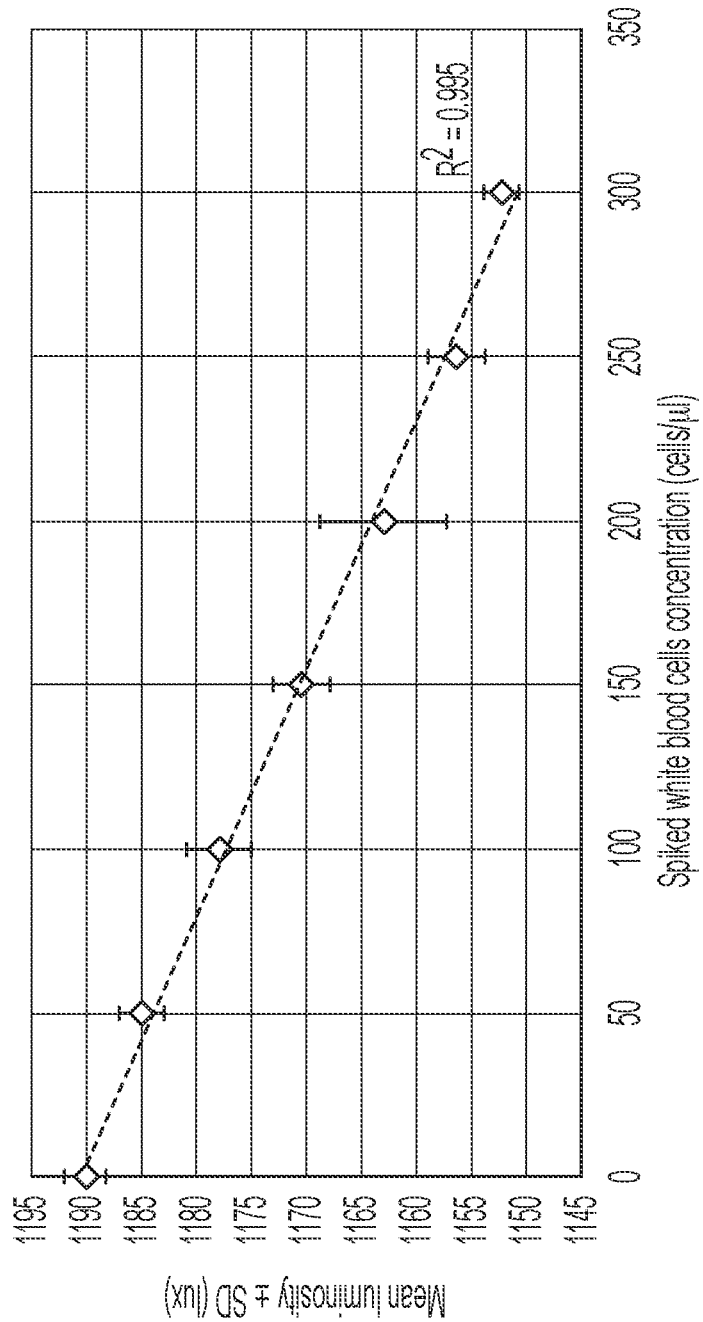
FIG. 11B shows another chart of test results demonstrating a correlation between relative luminosity and white blood cell concentration.

In an embodiment, the dialysate analysis device evaluates data received from the light sensor and/or one or more other sources (Operation 414). The dialysate analysis device may evaluate many different types of data to determine various properties (or suspected/predicted properties) of the spent dialysate. For example:

The dialysate analysis device may measure turbidity (i.e., loss of transparency) in the spent dialysate based on the relative luminosity or change in relative luminosity. Turbidity or relative luminosity can correlate with white blood cell concentrations. For example, FIGS. 11A and 11B show charts of test results demonstrating a correlation between relative luminosity and white blood cell concentration. The magnitude of a drop in transmittance through the spent dialysate, relative to transmittance in the absence of the spent dialysate (e.g., through clear air, water, or clean dialysate), can correlate with white blood cell concentrations. Thus, a drop in light transmittance through the spent dialysate may indicate an increase in white blood cells. Techniques described herein for measuring turbidity may be both more objective and more sensitive than traditional subjective techniques for assessing "cloudiness." Thus, techniques described herein may detect clinically significant levels of turbidity at a much earlier stage than traditional subjective approaches. For example, the International Society for Peritoneal Dialysis (IPSD) recommends that peritonitis be diagnosed when at least two of the following are present: (1) clinical features consistent with peritonitis (e.g., abdominal pain and/or cloudy dialysis effluent; (2) dialysis effluent white cell count >100/0 after a dwell time of at least 2 hours, with >50% polymorphonuclear WBC; and (3) positive dialysis effluent culture. In comparison, as shown in FIGS. 11A and 11B, one or more embodiments can detect white blood cell concentrations well below 100 per µl, using a light sensor as described herein.

The dialysate analysis device may use light scattering data to measure particle size and differentiate white blood cell species. Specifically, the light source may be a laser and the light sensor may sense scattering of the laser through the spent dialysate. Characteristics of the scattering may indicate particle sizes and/or be used to classify white blood cells. This approach may require a dark environment, to improve the light sensor's ability to detect the scattering. Certain classes of white blood cells and/or ratios thereof may indicate a higher likelihood of peritonitis. For example, if about half of the white blood cells in the spent dialysate are granulocytes, that ratio may be a strong indicator of peritonitis.

The dialysate analysis device may use data from a camera (e.g., a camera in a smartphone or tablet) to evaluate a lateral flow assay or dry chemistry test strip. Specifically, based on the appearance of the test strip as captured by the camera, the dialysate analysis device may measure leukocyte esterase as a surrogate for white blood cell concentration.

A Gram staining solution may have been mixed with the spent dialysate. The dialysate analysis device may use data from a microscope to examine the spent dialysate, to identify stained bacteria.

The dialysate analysis device may measure glucose concentration in dialysate. Specifically, a light source may emit near-infrared light, which may be used to detect glucose concentration in the dialysate. Glucose concentration may be used, for example, in calibration pre- and post-treatment. Specifically, the glucose (dextrose) concentration in fresh dialysate is known (e.g., 1.5%, 2.5%, 4.25%, or another known concentration). The near-infrared signal of dextrose at known concentrations may be predetermined, for example, in a lab setting. A patient's dialysate prescription may be obtained via manual user entry, by loading data from an electronic medical record, or from another source. For example, the dialysate analysis device may analyze a photo (e.g., perform text analysis, read a barcode, read a QR code, and/or perform another kind of analysis or combination thereof) of the fresh dialysate bag label captured by a smartphone camera or another kind of camera, to obtain information from the label about the patient's dialysate prescription. Thus, the near-infrared signal of dextrose in the patient's fresh dialysate, before dialysis, is known. The dialysate analysis device may obtain the near-infrared signal of dextrose in the spent dialysate, post-dialysis. In an embodiment, glucose content changes in dialysate, along with glucose levels in blood obtained by a glucometer, may be helpful to estimate transport status of the peritoneal membrane status. Because some patients have higher ultrafiltration volume than others, turbidity may be normalized by the volume of the spent dialysate.

The dialysate analysis device may evaluate a combination of data received from multiple sources. For example, if turbidity data indicates a white blood cell count greater than 100 per microliter, and light scattering data and/or lateral flow assay or dry chemistry test strip data indicate(s) that more than half are polymorphonuclear cells, the combination of data may suggest peritonitis.

In an embodiment, the dialysate analysis device determines whether an alert criterion is satisfied (Operation 416). An alert criterion is a rule that, when satisfied, indicates a condition that may require or benefit from human attention. For example, an alert criterion may indicate, based on evaluation of one or more types of data as described above, that the patient has an increased risk or likelihood of peritonitis. The increased risk or likelihood may be based on an absolute value (e.g., turbidity above a threshold amount, or a threshold ratio of granulocytes), a trend (e.g., turbidity or a ratio of a particular class of white blood cells increasing above a threshold rate), and/or another kind of metric or combination thereof.

In an embodiment, an alert criterion is a composite rule that combines one or multiple factors (e.g., turbidity, particle sizes, ratios of particle types, leukocyte esterase, presence of bacteria, and/or another factor or combination thereof) to compute the patient's risk or likelihood of having peritonitis and/or another condition. Additional factors may include, for example: social/environmental factors, such as smoking, living distantly from the peritoneal dialysis unit, and/or pets; medical factors such as obesity, depression, hypokalemia, hypoalbuminemia, absence of vitamin D supplementation, and/or invasive interventions (e.g., a colonoscopy); dialysis-related factors such as prior hemodialysis, peritoneal dialysis against the patient's choice, training, bioincompatible fluids, and/or wet contamination; infection-related factors such as nasal *Staphylococcus aureus* carrier status and/or previous exit-site infection; and/or another factor or combination thereof. Still more factors may include, for example, whether the patient has taken a day off from peritoneal dialysis, whether the spent dialysate is from the first drain of an APD patient with a dry day, and/or how long the dwell time lasted. In some cases, one or more factors may indicate a likelihood that turbidity is caused by peritoneal debris, and rinsing may be suggested rather than any approaches directed to treating infection.

In an embodiment, the patient's risk or likelihood of a particular condition may be computed as a numerical score and compared with a threshold numerical value. If an alert criterion is satisfied, then the dialysate analysis device generates an alert (Operation 418). The alert may include a risk score, diagnosis, recommended course of action (e.g., antibiotic treatment or rinsing), and/or other information relating to peritoneal dialysis and/or other health concerns. In some cases, a recommended course of treatment may be informed by self-reported symptoms (e.g., symptoms gathered via a graphical user interface as described below). If test outcomes are positive for a medical condition (e.g., peritonitis) and self-reported symptoms also are positive for that condition, an appropriate treatment (e.g., antibiotics) may be recommended. If test outcomes are negative and symptoms also are negative, no treatment may be recommended. If test outcomes and symptoms are inconsistent with each other (i.e., one is positive for a condition and the other is negative for that condition), clinical evaluation may be recommended. Generating an alert may help ensure early detection and treatment of peritonitis and/or one or more other conditions associated with peritoneal dialysis. In some cases, generating an alert may prompt the application of further techniques to confirm the validity of the alert, for example, by sending the dialysate drain bag and/or some or all of the spent dialysate to a laboratory for further analysis.

2.3 User Interface

In an embodiment, a dialysate analysis device includes a user interface (e.g., user interface 111 discussed above with respect to FIG. 1A) that provides audio and/or visual cues to assist with analyzing spent dialysate in a drain bag. The user interface may present audio and/or visual cues to assist in aligning the dialysate analysis device, aligning the drain bag, calibrating the dialysate analysis device, taring the drain bag, and/or one or more operations described herein. In addition, the user interface may present alerts based on alert criteria. Alternatively or additionally, one or more aspects of a graphical user interface described herein may be included in the apparatus itself, e.g., using a display as illustrated in FIG. 12G.

FIGS. 5A-5I are illustrations of an example of a graphical user interface according to an embodiment. These illustrations are provided as examples only and should not be construed as limiting one or more embodiments. In this example, the graphical user interface is generated by a software application executing in a smartphone.

Figure 5A:
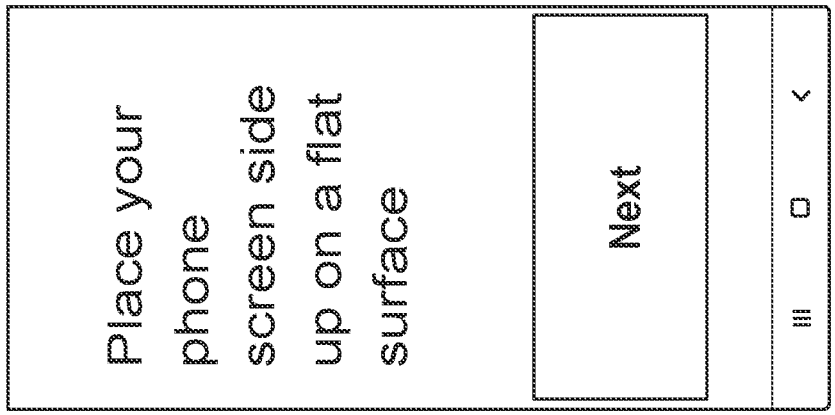
FIGS. 5A-5I are illustrations of an example of a graphical user interface according to an embodiment.
Figure 5B:
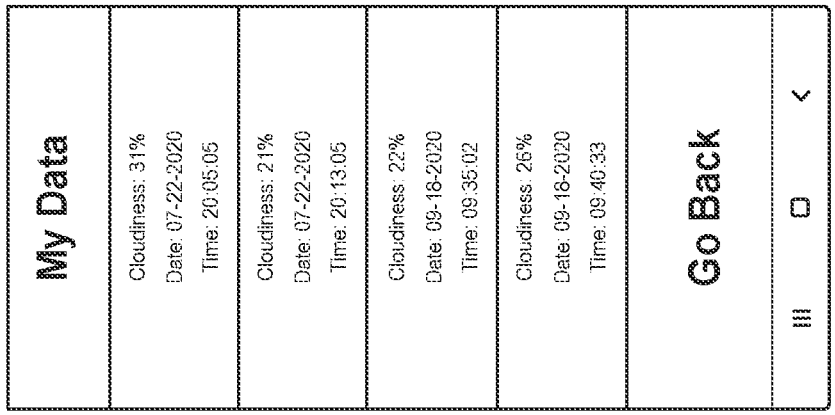
Figure 5C:
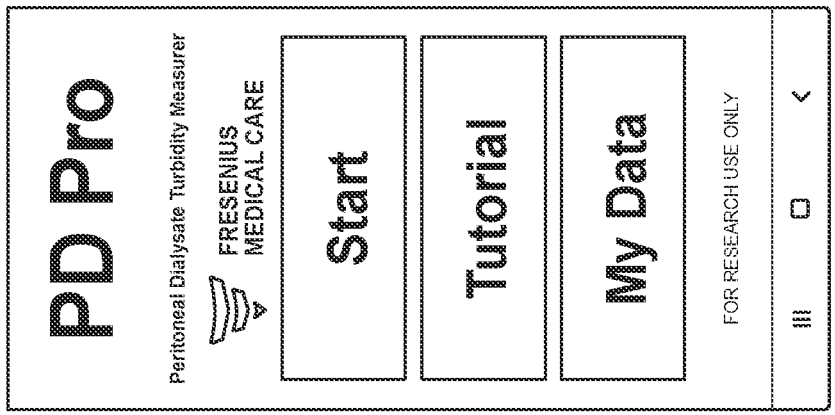
Figure 5F:
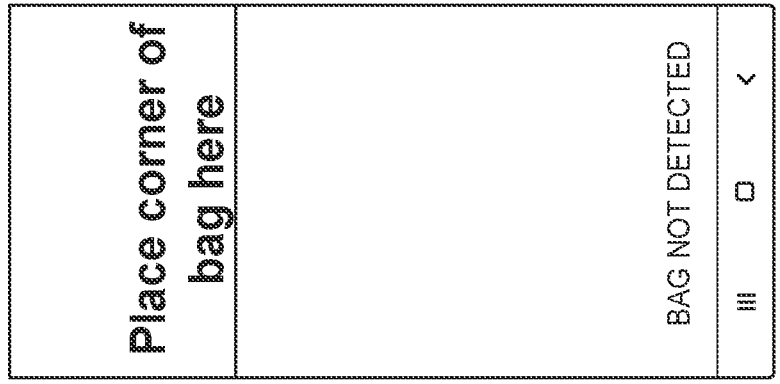
Figure 5E:
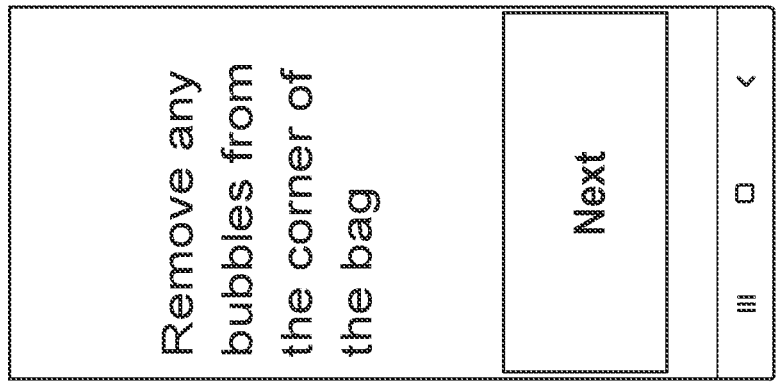
Figure 5D:
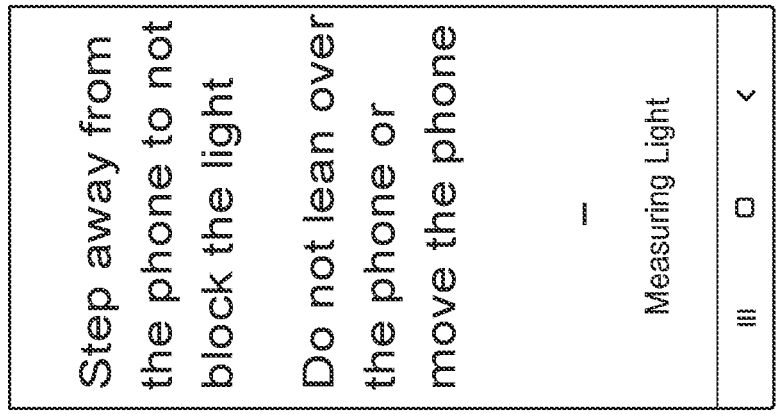
Figure 5I:
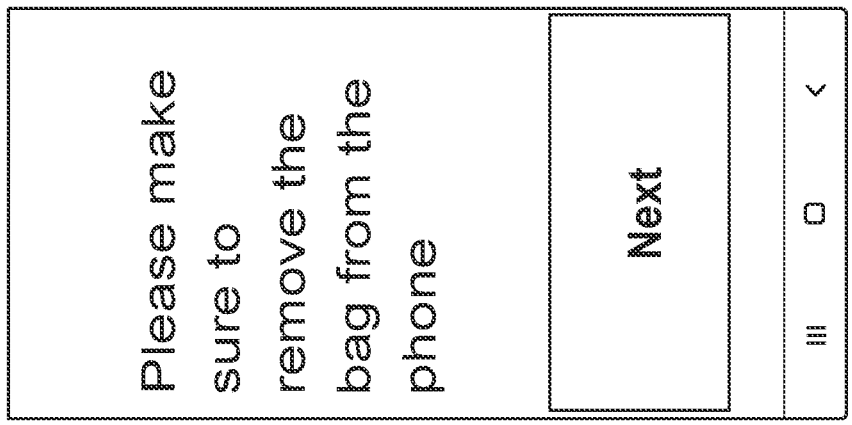
Figure 5H:
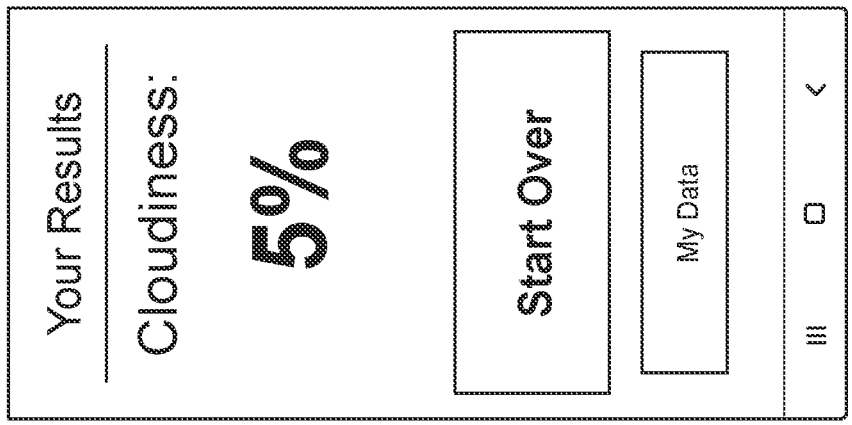
Figure 5G:
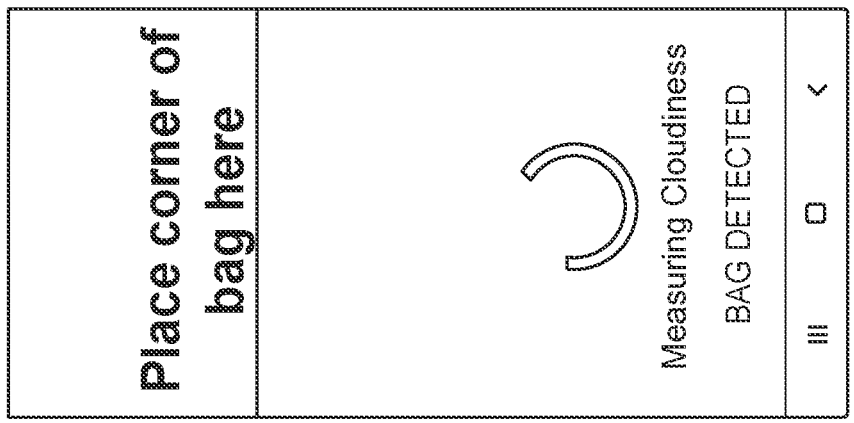

FIG. 5A illustrates an example of the graphical user interface (in this example, displayed on a mobile phone) presenting a feature menu to a user. In this example, the graphical user interface provides access to "start" a process for analyzing spent dialysate, enter a "tutorial" mode (i.e., learning how to use the graphical user interface and/or apparatus), or view "my data," i.e., prior analysis results. FIG. 5B illustrates an example of such prior analysis results, including cloudiness metrics determined at specific dates and times. FIG. 5C illustrates an example of the graphical user interface presenting cues to assist with aligning the dialysate analysis device. In this example, the cues include visual instructions to place the dialysate analysis device on a flat surface. FIG. 5D illustrates an example of the graphical user interface presenting cues to assist with calibrating the dialysate analysis device. In this example, the cues include visual instructions to step away from the dialysate analysis device, to avoid casting a shadow while the dialysate analysis device takes a baseline light reading. FIG. E illustrates an example of the GUI presenting cues to help ensure that the drain bag is prepared for analysis, in this example by removing bubbles from the corner of the drain bag. FIG. 5F illustrates an example of the graphical user interface presenting cues to assist with aligning the drain bag. In this example, the cues include a visual guide for where the drain bag should be placed (i.e., over a region of the dialysate analysis device that includes a light sensor). In addition, the cues indicate whether the drain bag is detected in the correct position, e.g., based on a reading from a scale and/or the light sensor. FIG. 5G illustrates an example of the GUI presenting a progress indicator as the spent dialysate is analyzed. FIG. 5H illustrates an example of the graphical user interface presenting data gathered and/or computed while analyzing spent dialysate in the drain bag. In this example, the data includes a cloudiness percentage, with the options to repeat the process or view historical data. FIG. 5I illustrates an example of the graphical user interface presenting cues for the user to take action(s) after the analysis is complete, in this example to be sure to remove the drain bag from atop the dialysate analysis device.

In an embodiment, a user interface that provides audio and/or visual cues helps ensure more accurate dialysate analysis, and/or more consistent dialysate analysis over multiple uses, than if a patient or other human operators were not provided with such cues.

3. Analyzing Spent Dialysate Along a Drain Line

In an embodiment, an apparatus is provided that facilitates placement of a light sensor relative to spent dialysate along a drain line (e.g., a clear section of drain line tubing or a light-permeable chamber positioned along the drain line). Specifically, the apparatus may help ensure that the light sensor is positioned, relative to a clear section of the drain line, drain line visualization chamber, or light-permeable chamber, in a configuration that helps ensure accurate and consistent light readings. In the following example, the light sensor is assumed to be part of a device separate from the dialysate analysis device. In other examples (not shown), the light sensor may be part of the dialysate analysis device.

3.1 Apparatus

Figure 6A:
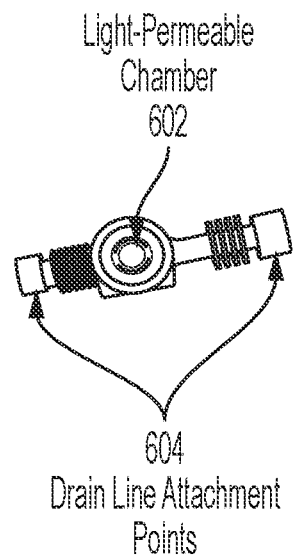
FIG. 6A is an illustration of an example of a light-permeable chamber according to an embodiment.
Figure 6B:
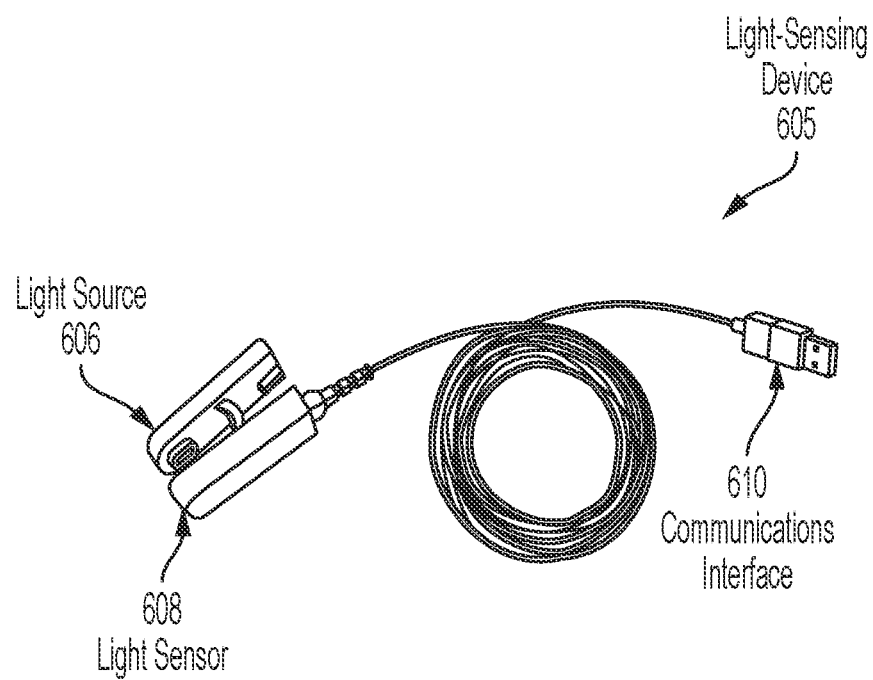
FIG. 6B is an illustration of an example of a light-sensing device according to an embodiment.

FIG. 6A is an illustration of an example of a light-permeable chamber 602 according to an embodiment. The light-permeable chamber 602 is installable along a drain line using drain line attachment points 604. The drain line attachment points 604 are configured to attach to reciprocal attachment points (not shown) in the drain line itself. Traditional drain lines do not include such attachment points. Thus, using the light-permeable chamber 602 may require a non-traditional drain line that is configured to accommodate the light-permeable chamber 602. To calibrate a light-sensing device for use with the light-permeable chamber 602, the light-sensing device may first be fastened (e.g., clamped) to a calibration chamber or other light-permeable component (not shown) that may be made, for example, of layered plastic or glass having known optical qualities. Sensing light through a calibration chamber may allow for calibration to a baseline state prior to using the light-permeable chamber 602 to analyze spent dialysate.

FIG. 6B is an illustration of an example of a light-sensing device 605 according to an embodiment. Specifically, FIG. 6B illustrates an example of a light-sensing device 605 configured to emit and detect light through a light-permeable chamber, such as the example light-permeable chamber 602 illustrated in FIG. 6A. The light-sensing device 605 includes a light source 606 and a light sensor 608, disposed on opposing sides of a clamping mechanism (e.g., a clip). The clamping mechanism is configured so that when the light-sensing device 605 is clamped to the light-permeable chamber, light emitted by the light source 606 is directed toward, or approximately toward, the light sensor 608. The light source 606 may be configured to emit a single wavelength of light or multiple wavelengths of light. The light sensor 608 may be configured to sense a single wavelength of light or multiple wavelengths of light. The light-sensing device 605 is configured to transmit data from the light sensor 608 to a dialysate analysis device via a communications interface 610, which in this example is a USB cable.

In an embodiment, the light-permeable chamber 602 and/or light-sensing device 605 are similar in construction to equipment used to measure blood properties such as hematocrit, percent change in blood volume, and/or oxygen saturation. For example, the light-permeable chamber 602 may be similar in construction to a Crit-Line blood chamber manufactured by Fresenius Medical Care, which is typically used with a Crit-Line III monitor also manufactured by Fresenius Medical Care. The light-permeable chamber 602 may include structural modifications from the blood chamber construction, for example to allow the light-permeable chamber 602 to be positioned along the drain line. The light-sensing device 605 may be a CLiC™ device manufactured by Fresenius Medical Care, which is designed to clamp onto a Crit-Line blood chamber. The Crit-Line blood chamber and CLiC™ device are designed for mutual compatibility. Specifically, the Crit-Line blood chamber has flat external surfaces that accommodate the CLiC™ device's light source 606 and light sensor 608 in approximately parallel and opposing positions, such that light from the light source 606 is directed through the chamber toward the light sensor 608. Modifying and/or repurposing existing equipment that is typically used in blood analysis may provide cost savings to a company manufacturing the equipment, while extending the equipment's utility to unconventional dialysate analysis techniques described herein.

In an embodiment, the light-permeable chamber 602 is a removable, disposable, single- or multiple-use chamber. Alternatively, the light-permeable chamber 602 may be fixed to the drain line and/or designed for multiple uses prior to disposal.

While examples are described above with reference to the illustrations of FIGS. 6A-6B, a light-sensing device may take another form. For example, a light-sensing device may include an enclosure (e.g., a cuboid enclosure) configured to be attached or otherwise positioned along a drain line (e.g., over a drain line visualization chamber, light-permeable chamber, or a clear section of the drain line). One or more light sources and one or more light sensors may be disposed within the enclosure. The enclosure may help avoid light contamination from sources other than a light source contained within the enclosure.

3.2 Method

Figure 7:
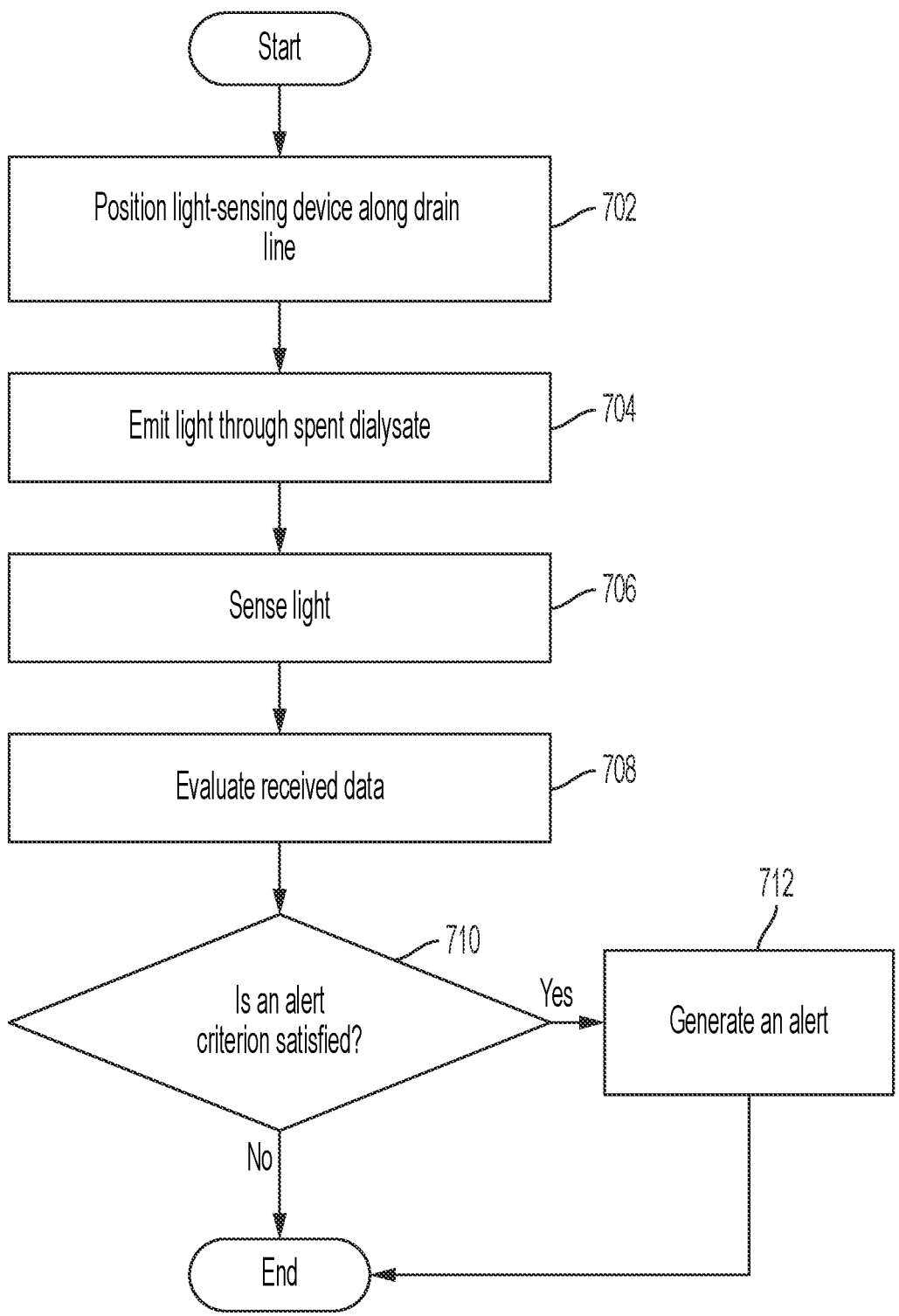
FIG. 7 is a flow diagram of an example of operations for analyzing spent dialysate along a drain line according to an embodiment.

FIG. 7 is a flow diagram of an example of operations for analyzing spent dialysate along a drain line according to an embodiment. One or more operations illustrated in FIG. 7 may be modified, rearranged, or omitted all together. Accordingly, the particular sequence of operations illustrated in FIG. 7 should not be construed as limiting the scope of one or more embodiments.

In an embodiment, a light-sensing device (e.g., the example light-sensing device 605 illustrated in FIG. 6B) is positioned along a drain line. The light-sensing device may be positioned, for example, at a clear section of the drain line or a light-permeable chamber (e.g., the example light-permeable chamber 602 illustrated in FIG. 6A). The light-sensing device is positioned so that when light is emitted through the spent dialysate draining through the drain line (by a light source that is part of the light-sensing device or from another source), a light sensor in the light-sensing device is able to sense the emitted light.

In an embodiment, light is emitted through the spent dialysate (Operation 704). Specifically, light is emitted through the clear section of the drain line, drain line visualization chamber, or light-permeable chamber where the light-sensing device is situated. The light emitted through the spent dialysate may be ambient light (e.g., from sunlight and/or one or more general-purpose lamps) in the environment. Alternatively, a dedicated light source may emit light through the spent dialysate (for example, one or more light sources 606 of a light-sensing device 605 as illustrated in FIG. 6B). As discussed above, a dedicated light source may emit light responsive to an electrical signal or other type of instruction transmitted by the dialysate analysis device.

In an embodiment, a light sensor in the light-sensing device senses the light emitted through the spent dialysate (Operation 706). Specifically, the light sensor senses light emitted at one or more particular wavelengths used to analyze the spent dialysate. As discussed above, the light sensor may sense the light responsive to an electrical signal or other type of instruction transmitted by the dialysate analysis device. The light sensor may sense the light in a single reading. Alternatively, the light sensor may take multiple readings. When evaluating data received from the light sensor as described below, the dialysate analysis device may determine an average, mean, or other statistic based on multiple readings. In addition, the dialysate analysis device may discard outliers that deviate significantly from an average, mean, or other reference value.

In an embodiment, the dialysate analysis device evaluates data received from the light sensor and/or one or more other sources (Operation 708). The dialysate analysis device may determine whether an alert criterion is satisfied (Operation 710). If an alert criterion is satisfied, then the dialysate analysis device may generate an alert (Operation 712). Evaluating data, determining whether an alert criterion is satisfied, and generating an alert may be performed as described above with respect to FIG. 4.

4. User Interface for Patient Tracking

In an embodiment, a dialysate analysis device (and/or the apparatus itself) includes hardware, firmware, and/or software that tracks a patient's history, which may include a history of any type of measurement and/or computation described herein. The history may also include self-reported data, such as symptoms, urine volume, etc. The patient's history may be uploaded and saved to the patient's electronic health record. The dialysate analysis device and/or apparatus may be configured to present information about patient tracking in a user interface (e.g., user interface 111 discussed above with respect to FIG. 1A, and/or a digital display as illustrated in FIG. 12G). Alternatively or additionally, the dialysate analysis device may be configured to present a user interface to obtain user input that assists with patient tracking and/or diagnosis. FIGS. 8A-8E are illustrations of an example of a graphical user interface for patient tracking according to an embodiment. These illustrations are provided as examples only and should not be construed as limiting one or more embodiments. In this example, the graphical user interface is generated by a software application executing in a smartphone.

Figure 8A:
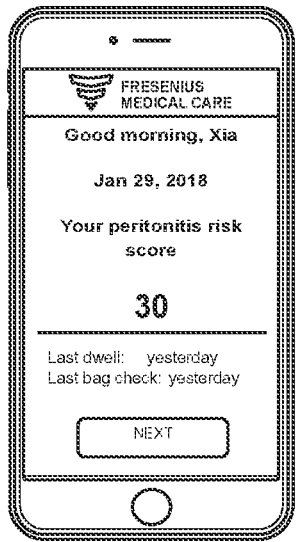
FIGS. 8A-8E are illustrations of another example of a graphical user interface according to an embodiment.
Figure 8B:
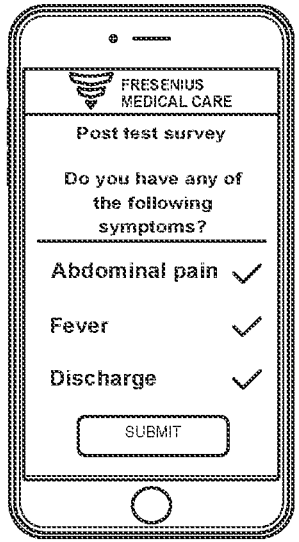
Figure 8C:
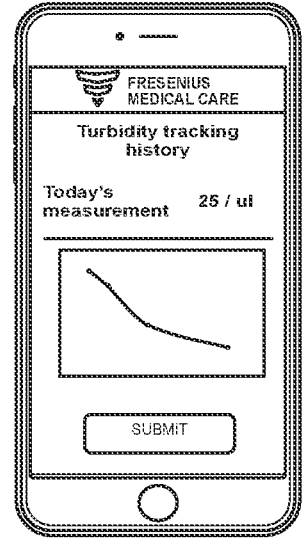
Figure 8D:
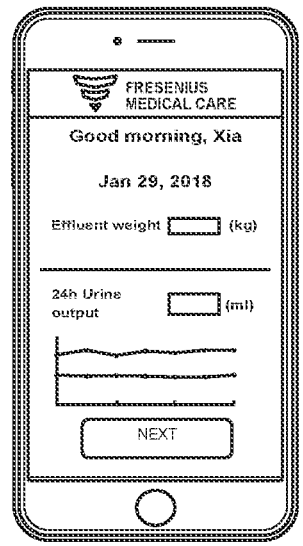
Figure 8E:

FIG. 8A illustrates an example of the graphical user interface presenting a patient's risk score, that quantifies the patient's risk or likelihood of peritonitis. A risk score may be calculated as described above. In this example, the risk score is a numerical score. FIG. 8B illustrates an example of the graphical user interface presenting user interface controls that allow a patient to indicate any symptoms (e.g. peritonitis-related symptoms) that they may be experiencing. The dialysate analysis device may store a history of such symptoms. Alternatively or additionally, certain symptoms may trigger an alert indicating a risk of peritonitis. Symptoms may be compared with test results to determine a recommended course of action (e.g., treatment or clinical follow-up), as described above. FIG. 8C illustrates an example of the graphical user interface presenting a history of spent dialysate turbidity. The history may help a patient or other human operator identify, for example, trends that may indicate improving or worsening health conditions. For example, if a clear drain bag is not present within a threshold amount of time following a treatment (e.g., five days after starting an antibiotic treatment), further clinical attention may be required. As another example, a trend of declining white blood cell counts may indicate that a treatment was successful. If a trend is not as expected (e.g., white blood cells do not decline as quickly as expected), then treatment may be adjusted (e.g., by adjusting antibiotics types and/or dosage) while the treatment is still ongoing. Similarly, FIG. 8D illustrates an example of the graphical user interface presenting user interface controls that allow a patient to enter effluent weight and urine output, while also presenting trends. FIG. 8E illustrates an example of the graphical user interface presenting a gamification interface, i.e., an interface that allows the patient or other human operator to earn "points" (in this case, stars) as rewards for completing certain challenges and/or objectives. For example, stars may be awarded each time the dialysate analysis device is used to analyze spent dialysate, to help encourage consistent health monitoring. As illustrated in FIG. 8E, the gamification feature may include a social component, where the user is compared with one or more friends/contacts participating in the same challenge(s) and/or objective(s). In general, gamification may be associated with improved treatment compliance.

5. Miscellaneous; Extensions

In an embodiment, a system includes one or more devices, including one or more hardware processors, that are configured to perform any of the operations described herein and/or recited in any of the claims.

In an embodiment, a non-transitory computer-readable storage medium stores instructions that, when executed by one or more hardware processors, cause performance of any of the operations described herein and/or recited in any of the claims.

Any combination of the features and functionalities described herein may be used in accordance with an embodiment. In the foregoing specification, embodiments have been described with reference to numerous specific details that may vary from implementation to implementation. Accordingly, the specification and figures are to be regarded in an illustrative rather than a restrictive sense. The sole and exclusive indicator of the scope of the invention, and what is intended by the Applicant to be the scope of the invention, is the literal and equivalent scope of the set of claims that issue from this application, in the specific form in which such claims issue, including any subsequent correction.

6. Computing Devices

In an embodiment, techniques described herein are implemented by one or more special-purpose computing devices (i.e., computing devices specially configured to perform certain functionality). The special-purpose computing device(s) may be hard-wired to perform the techniques and/or may include digital electronic devices such as one or more application-specific integrated circuits (ASICs), field programmable gate arrays (FPGAs), and/or network processing units (NPUs) that are persistently programmed to perform the techniques. Alternatively or additionally, a computing device may include one or more general-purpose hardware processors programmed to perform the techniques pursuant to program instructions in firmware, memory, and/or other storage. Alternatively or additionally, a special-purpose computing device may combine custom hard-wired logic, ASICs, FPGAs, or NPUs with custom programming to accomplish the techniques. A special-purpose computing device may include a desktop computer system, portable computer system, handheld device, networking device, and/or any other device(s) incorporating hard-wired and/or program logic to implement the techniques.

Figure 9:
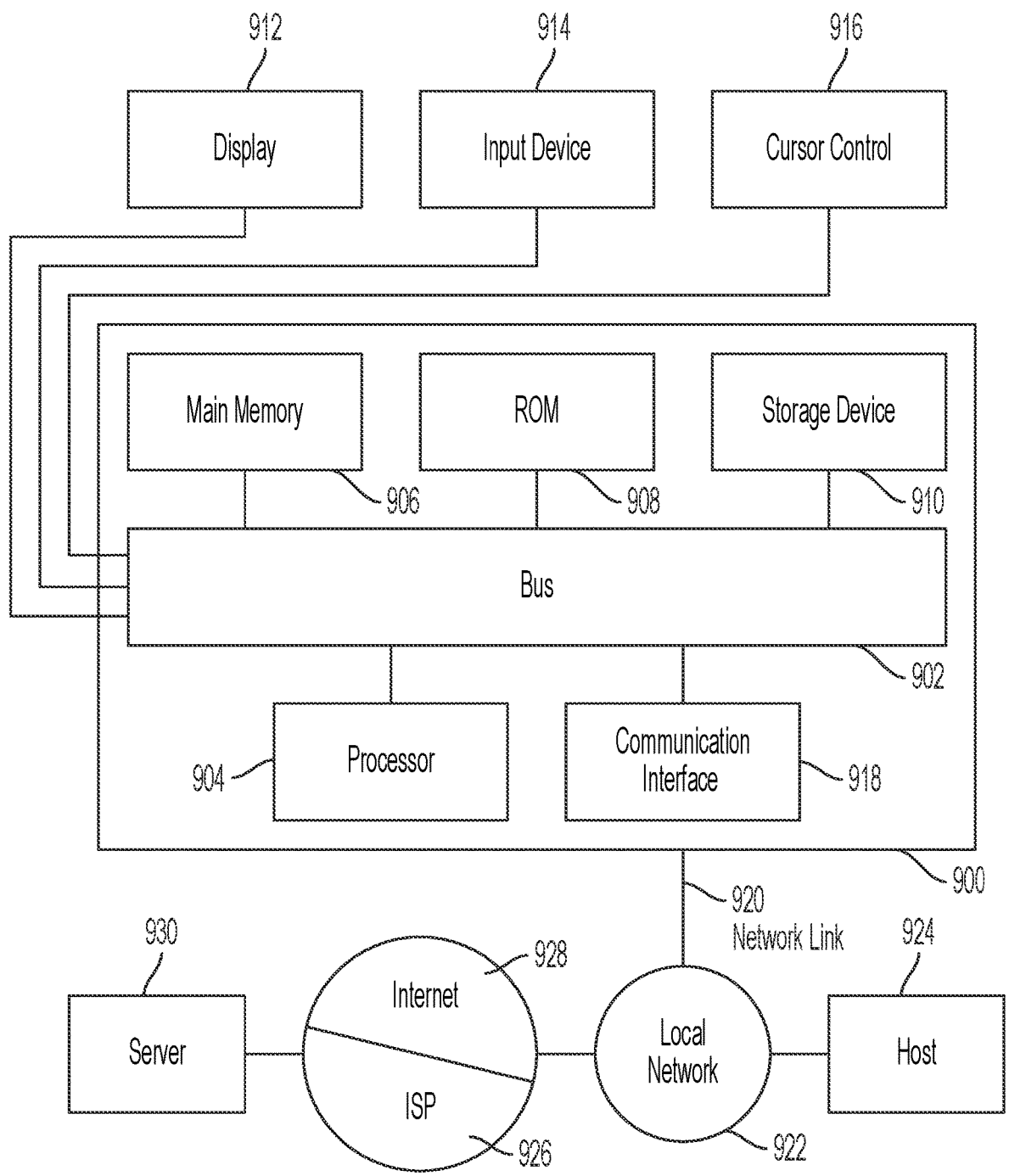
FIG. 9 is a block diagram of an example of a computer system according to an embodiment.

For example, FIG. 9 is a block diagram of an example of a computer system 900 according to an embodiment. Computer system 900 includes a bus 902 or other communication mechanism for communicating information, and a hardware processor 904 coupled with the bus 902 for processing information. Hardware processor 904 may be a general-purpose microprocessor.

Computer system 900 also includes a main memory 906, such as a random access memory (RAM) or other dynamic storage device, coupled to bus 902 for storing information and instructions to be executed by processor 904. Main memory 906 also may be used for storing temporary variables or other intermediate information during execution of instructions to be executed by processor 904. Such instructions, when stored in one or more non-transitory storage media accessible to processor 904, render computer system 900 into a special-purpose machine that is customized to perform the operations specified in the instructions.

Computer system 900 further includes a read only memory (ROM) 908 or other static storage device coupled to bus 902 for storing static information and instructions for processor 904. A storage device 910, such as a magnetic disk or optical disk, is provided and coupled to bus 902 for storing information and instructions.

Computer system 900 may be coupled via bus 902 to a display 912, such as a liquid crystal display (LCD), plasma display, electronic ink display, cathode ray tube (CRT) monitor, or any other kind of device for displaying information to a computer user. An input device 914, including alphanumeric and other keys, may be coupled to bus 902 for communicating information and command selections to processor 904. Alternatively or additionally, computer system 900 may receive user input via a cursor control 916, such as a mouse, a trackball, a trackpad, or cursor direction keys for communicating direction information and command selections to processor 904 and for controlling cursor movement on display 912. This input device typically has two degrees of freedom in two axes, a first axis (e.g., x) and a second axis (e.g., y), that allows the device to specify positions in a plane. Alternatively or additionally, computer system 9 may include a touchscreen. Display 912 may be configured to receive user input via one or more pressure-sensitive sensors, multi-touch sensors, and/or gesture sensors. Alternatively or additionally, computer system 900 may receive user input via a microphone, video camera, and/or some other kind of user input device (not shown).

Computer system 900 may implement the techniques described herein using customized hard-wired logic, one or more ASICs or FPGAs, firmware, and/or program logic which in combination with other components of computer system 900 causes or programs computer system 900 to be a special-purpose machine. According to one embodiment, the techniques herein are performed by computer system 900 in response to processor 904 executing one or more sequences of one or more instructions contained in main memory 906. Such instructions may be read into main memory 906 from another storage medium, such as storage device 910. Execution of the sequences of instructions contained in main memory 906 causes processor 904 to perform the process steps described herein. Alternatively or additionally, hard-wired circuitry may be used in place of or in combination with software instructions.

The term "storage media" as used herein refers to one or more non-transitory media storing data and/or instructions that cause a machine to operate in a specific fashion. Such storage media may comprise non-volatile media and/or volatile media. Non-volatile media includes, for example, optical or magnetic disks, such as storage device 910. Volatile media includes dynamic memory, such as main memory 906. Common forms of storage media include, for example, a floppy disk, a flexible disk, hard disk, solid state drive, magnetic tape or other magnetic data storage medium, a CD-ROM or any other optical data storage medium, any physical medium with patterns of holes, a RAM, a programmable read-only memory (PROM), an erasable PROM (EPROM), a FLASH-EPROM, non-volatile random-access memory (NVRAM), any other memory chip or cartridge, content-addressable memory (CAM), and ternary content-addressable memory (TCAM).

A storage medium is distinct from but may be used in conjunction with a transmission medium. Transmission media participate in transferring information between storage media. Examples of transmission media include coaxial cables, copper wire, and fiber optics, including the wires that comprise bus 902. Transmission media may also take the form of acoustic or light waves, such as those generated during radio-wave and infra-red data communications.

Various forms of media may be involved in carrying one or more sequences of one or more instructions to processor 904 for execution. For example, the instructions may initially be carried on a magnetic disk or solid state drive of a remote computer. The remote computer may load the instructions into its dynamic memory and send the instructions over a network, via a network interface controller (NIC), such as an Ethernet controller or Wi-Fi controller. A NIC local to computer system 900 may receive the data from the network and place the data on bus 902. Bus 902 carries the data to main memory 906, from which processor 904 retrieves and executes the instructions. The instructions received by main memory 906 may optionally be stored on storage device 910 either before or after execution by processor 904.

Computer system 900 also includes a communication interface 918 coupled to bus 902. Communication interface 918 provides a two-way data communication coupling to a network link 920 that is connected to a local network 922. For example, communication interface 918 may be an integrated services digital network (ISDN) card, cable modem, satellite modem, or a modem to provide a data communication connection to a corresponding type of telephone line. As another example, communication interface 918 may be a local area network (LAN) card to provide a data communication connection to a compatible LAN. Wireless links may also be implemented. In any such implementation, communication interface 918 sends and receives electrical, electromagnetic or optical signals that carry digital data streams representing various types of information.

Network link 920 typically provides data communication through one or more networks to other data devices. For example, network link 920 may provide a connection through local network 922 to a host computer 924 or to data equipment operated by an Internet Service Provider (ISP) 926. ISP 926 in turn provides data communication services through the world wide packet data communication network now commonly referred to as the "Internet" 928. Local network 922 and Internet 928 both use electrical, electromagnetic or optical signals that carry digital data streams. The signals through the various networks and the signals on network link 920 and through communication interface 918, which carry the digital data to and from computer system 900, are example forms of transmission media.

Computer system 900 can send messages and receive data, including program code, through the network(s), network link 920 and communication interface 918. In the Internet example, a server 930 might transmit a requested code for an application program through Internet 928, ISP 926, local network 922, and communication interface 918.

The received code may be executed by processor 904 as it is received, and/or stored in storage device 910, or other non-volatile storage for later execution.

7. Computer Networks

In an embodiment, a computer network provides connectivity among a set of nodes running software that utilizes techniques as described herein. The nodes may be local to and/or remote from each other. The nodes are connected by a set of links. Examples of links include a coaxial cable, an unshielded twisted cable, a copper cable, an optical fiber, and a virtual link.

A subset of nodes implements the computer network. Examples of such nodes include a switch, a router, a firewall, and a network address translator (NAT). Another subset of nodes uses the computer network. Such nodes (also referred to as "hosts") may execute a client process and/or a server process. A client process makes a request for a computing service (for example, a request to execute a particular application and/or retrieve a particular set of data). A server process responds by executing the requested service and/or returning corresponding data.

A computer network may be a physical network, including physical nodes connected by physical links. A physical node is any digital device. A physical node may be a function-specific hardware device. Examples of function-specific hardware devices include a hardware switch, a hardware router, a hardware firewall, and a hardware NAT. Alternatively or additionally, a physical node may be any physical resource that provides compute power to perform a task, such as one that is configured to execute various virtual machines and/or applications performing respective functions. A physical link is a physical medium connecting two or more physical nodes. Examples of links include a coaxial cable, an unshielded twisted cable, a copper cable, and an optical fiber.

A computer network may be an overlay network. An overlay network is a logical network implemented on top of another network (for example, a physical network). Each node in an overlay network corresponds to a respective node in the underlying network. Accordingly, each node in an overlay network is associated with both an overlay address (to address the overlay node) and an underlay address (to address the underlay node that implements the overlay node). An overlay node may be a digital device and/or a software process (for example, a virtual machine, an application instance, or a thread). A link that connects overlay nodes may be implemented as a tunnel through the underlying network. The overlay nodes at either end of the tunnel may treat the underlying multi-hop path between them as a single logical link. Tunneling is performed through encapsulation and decapsulation.

In an embodiment, a client may be local to and/or remote from a computer network. The client may access the computer network over other computer networks, such as a private network or the Internet. The client may communicate requests to the computer network using a communications protocol, such as Hypertext Transfer Protocol (HTTP). The requests are communicated through an interface, such as a client interface (such as a web browser), a program interface, or an application programming interface (API).

In an embodiment, a computer network provides connectivity between clients and network resources. Network resources include hardware, firmware, and/or software configured to execute server processes. Examples of network resources include a processor, a data storage, a virtual machine, a container, and/or a software application. Network resources may be shared amongst multiple clients. Clients request computing services from a computer network independently of each other. Network resources are dynamically assigned to the requests and/or clients on an on-demand basis. Network resources assigned to each request and/or client may be scaled up or down based on, for example, (a) the computing services requested by a particular client, (b) the aggregated computing services requested by a particular tenant, and/or (c) the aggregated computing services requested of the computer network. Such a computer network may be referred to as a "cloud network."

In an embodiment, a service provider provides a cloud network to one or more end users. Various service models may be implemented by the cloud network, including but not limited to Software-as-a-Service (SaaS), Platform-as-a-Service (PaaS), and Infrastructure-as-a-Service (IaaS). In SaaS, a service provider provides end users the capability to use the service provider's applications, which are executing on the network resources. In PaaS, the service provider provides end users the capability to deploy custom applications onto the network resources. The custom applications may be created using programming languages, libraries, services, and tools supported by the service provider. In IaaS, the service provider provides end users the capability to provision processing, storage, networks, and other fundamental computing resources provided by the network resources. Any applications, including an operating system, may be deployed on the network resources.

In an embodiment, various deployment models may be implemented by a computer network, including but not limited to a private cloud, a public cloud, and a hybrid cloud. In a private cloud, network resources are provisioned for exclusive use by a particular group of one or more entities (the term "entity" as used herein refers to a corporation, organization, person, or other entity). The network resources may be local to and/or remote from the premises of the particular group of entities. In a public cloud, cloud resources are provisioned for multiple entities that are independent from each other (also referred to as "tenants" or "customers"). In a hybrid cloud, a computer network includes a private cloud and a public cloud. An interface between the private cloud and the public cloud allows for data and application portability. Data stored at the private cloud and data stored at the public cloud may be exchanged through the interface. Applications implemented at the private cloud and applications implemented at the public cloud may have dependencies on each other. A call from an application at the private cloud to an application at the public cloud (and vice versa) may be executed through the interface.

In an embodiment, a system supports multiple tenants. A tenant is a corporation, organization, enterprise, business unit, employee, or other entity that accesses a shared computing resource (for example, a computing resource shared in a public cloud). One tenant (through operation, tenant-specific practices, employees, and/or identification to the external world) may be separate from another tenant. The computer network and the network resources thereof are accessed by clients corresponding to different tenants. Such a computer network may be referred to as a "multi-tenant computer network." Several tenants may use a same particular network resource at different times and/or at the same time. The network resources may be local to and/or remote from the premises of the tenants. Different tenants may demand different network requirements for the computer network. Examples of network requirements include processing speed, amount of data storage, security requirements, performance requirements, throughput requirements, latency requirements, resiliency requirements, Quality of Service (QoS) requirements, tenant isolation, and/or consistency. The same computer network may need to implement different network requirements demanded by different tenants.

In an embodiment, in a multi-tenant computer network, tenant isolation is implemented to ensure that the applications and/or data of different tenants are not shared with each other. Various tenant isolation approaches may be used. In an embodiment, each tenant is associated with a tenant ID. Applications implemented by the computer network are tagged with tenant ID's. Additionally or alternatively, data structures and/or datasets, stored by the computer network, are tagged with tenant ID's. A tenant is permitted access to a particular application, data structure, and/or dataset only if the tenant and the particular application, data structure, and/or dataset are associated with a same tenant ID. As an example, each database implemented by a multi-tenant computer network may be tagged with a tenant ID. Only a tenant associated with the corresponding tenant ID may access data of a particular database. As another example, each entry in a database implemented by a multi-tenant computer network may be tagged with a tenant ID. Only a tenant associated with the corresponding tenant ID may access data of a particular entry. However, the database may be shared by multiple tenants. A subscription list may indicate which tenants have authorization to access which applications. For each application, a list of tenant ID's of tenants authorized to access the application is stored. A tenant is permitted access to a particular application only if the tenant ID of the tenant is included in the subscription list corresponding to the particular application.

In an embodiment, network resources (such as digital devices, virtual machines, application instances, and threads) corresponding to different tenants are isolated to tenant-specific overlay networks maintained by the multi-tenant computer network. As an example, packets from any source device in a tenant overlay network may only be transmitted to other devices within the same tenant overlay network. Encapsulation tunnels may be used to prohibit any transmissions from a source device on a tenant overlay network to devices in other tenant overlay networks. Specifically, the packets, received from the source device, are encapsulated within an outer packet. The outer packet is transmitted from a first encapsulation tunnel endpoint (in communication with the source device in the tenant overlay network) to a second encapsulation tunnel endpoint (in communication with the destination device in the tenant overlay network). The second encapsulation tunnel endpoint decapsulates the outer packet to obtain the original packet transmitted by the source device. The original packet is transmitted from the second encapsulation tunnel endpoint to the destination device in the same particular overlay network.

8. Connected Health System

Figure 10:
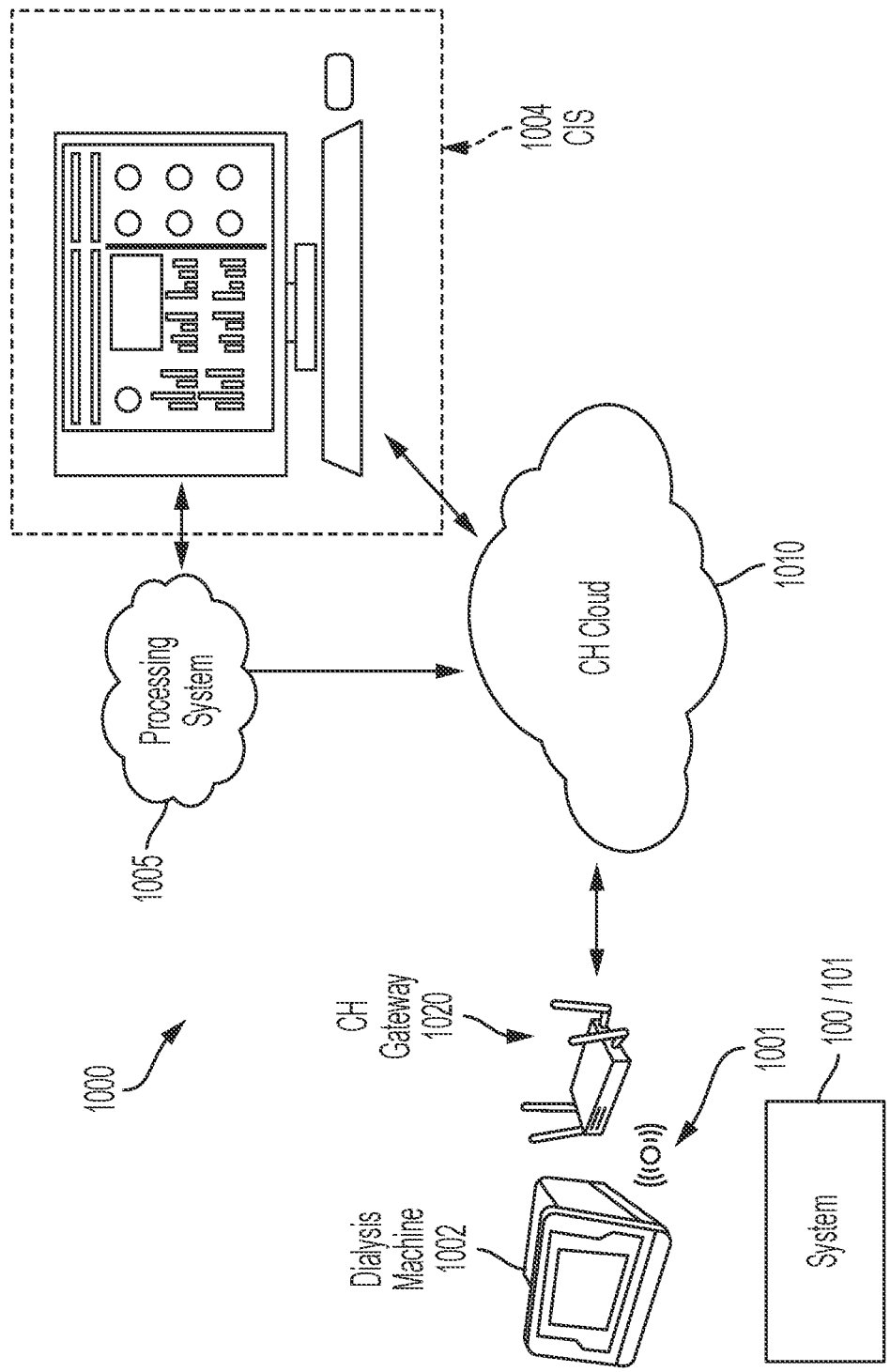
FIG. 10 is a block diagram of an example of a connected health system according to an embodiment.

Systems 100 and 101, as described herein, may configured to be part of or communicate with a connected health (CH) system 1000. FIG. 10 is a schematic illustration showing an example of a connected health (CH) system 1000 that may include, among other things, a processing system 1005, a CH cloud service 1010 and a gateway (CH Gateway) 1020 that may be used in connection with network aspects of the system described herein. The processing system 1005 may be a server and/or cloud-based system that processes, compatibility checks, and/or formats medical information, including prescription information generated at a clinical information system (CIS) 1004 of a clinic or hospital, in connection with data transmission operations of the CH system 1000. The CH system 1000 may include appropriate encryption and data security mechanisms. The CH cloud service 1010 may be a cloud-based application that serves as a communication pipeline (e.g., facilitates the transfer of data) among components of the CH system 1000 via connections to a network such as the Internet. The gateway 1020 may serve as a communication device facilitating communication among components of the CH system 1000. In various embodiments, the gateway 1020 may be in communication with a dialysis machine 1002 (e.g., PD cycler) and a system 100/101 via a wireless connection 1001, such as a Bluetooth, Wi-Fi, and/or other appropriate type of local or short range wireless connection. The gateway 1020 may also be in connection with the CH cloud service 1010 via a secure network (e.g., Internet) connection. The gateway 1020 may be configured to transmit/receive data to/from the CH cloud service 1010 and transmit/receive data to/from the dialysis machine 1002 and system 100/101. The dialysis machine 1002 may poll the CH cloud service 1010 for available files (e.g., via the gateway 320), and the dialysis machine 1002 and/or system 100/101 may temporarily store available files for processing.

What is claimed is:

1. An apparatus comprising:
a base;
one or more sides coupled to the base, the base and the one or more sides configured to accommodate a dialysate drain bag in a predetermined position;
a light source hingedly coupled to the base and configured to be selectively positioned to emit light through the dialysate drain bag;
a light sensor coupled to the base and positioned to sense light emitted by the light source through the dialysate drain bag;
one or more processors; and
one or more non-transitory computer-readable media storing instructions that, when executed by the one or more processors, cause the one or more processors to perform operations comprising analyzing spent dialysate in the dialysate drain bag based at least on the light sensed by the light sensor.

2. The apparatus of claim 1, further comprising:
a display,
the operations further comprising presenting an alert on the display when the spent dialysate satisfies an alert condition.

3. The apparatus of claim 2 wherein the display is coupled to the light source on a side of the light source furthest from the base.

4. The apparatus of claim 1, further comprising:
a scale configured to measure a weight of the dialysate drain bag when the dialysate drain bag is in the predetermined position,
analyzing the spent dialysate being further based on the weight of the dialysate drain bag.

5. The apparatus of claim 4, wherein the scale is a hook scale.

6. The apparatus of claim 4 wherein the one or more processors further are configured to assume a depth of the dialysate drain bag based on the weight.

7. The apparatus of claim 4 wherein the scale includes one or more force sensitive resistors configured to sense a weight of the dialysate drain bag when the dialysate drain bag rests on the base.

8. The apparatus of claim 1, the base and one or more sides being configured to accommodate the dialysate drain bag in the predetermined position while the dialysate drain bag is hanging from a hook scale.

9. The apparatus of claim 1, analyzing the spent dialysate comprising one or more of:
measuring turbidity of the spent dialysate;
estimating glucose concentration in the spent dialysate;
estimating a proportion of white blood cells in the spent dialysate; or
estimating a proportion of polymorphonuclear cells in the spent dialysate.

10. The apparatus of claim 1, analyzing the spent dialysate comprising estimating a risk of peritonitis.

11. The apparatus of claim 1, analyzing the spent dialysate comprising transmitting data to a server and receiving an analysis result from the server.

12. The apparatus of claim 1, the light sensor being one of a plurality of light sensors collectively configured to sense light at two or more of near-infrared, ultraviolet, visible, or fluorescent light.

13. The apparatus of claim 1, the light source being disposed in a hinged portion of the apparatus, so that the light source can be moved to accommodate placement of the dialysate drain bag in the predetermined position.

14. The apparatus of claim 1 wherein the light source is pivotably coupled to the base.

15. The apparatus of claim 14 further comprising a hinge coupled between the light source and the base.

16. The apparatus of claim 1 wherein the light sensor is coupled to the base such that the dialysate drain bag rests above the light sensor on the base.

17. The apparatus of claim 16 wherein the light source is above the light sensor and the dialysate drain bag, such that the light source emits light downward toward the base.

* * * * *